(12) United States Patent
van Milligen et al.

(10) Patent No.: US 7,744,907 B2
(45) Date of Patent: Jun. 29, 2010

(54) EX VIVO ANIMAL OR CHALLENGE MODEL AS METHOD TO MEASURE PROTECTIVE IMMUNITY DIRECTED AGAINST PARASITES AND VACCINES SHOWN TO BE PROTECTIVE IN THE METHOD

(75) Inventors: Florine Johanna van Milligen, Abcoude (NL); Johannes Bernardus Wilhelmus Joseph Cornelissen, Dronten (NL); Bernard Adri Bokhout, Ermelo (NL)

(73) Assignee: Stichting Dienst Landbouwkundig Onderzoek, Wageningen (NL)

( * ) Notice: Subject to any disclaimer, the term of this patent is extended or adjusted under 35 U.S.C. 154(b) by 0 days.

(21) Appl. No.: 11/881,598

(22) Filed: Jul. 26, 2007

(65) Prior Publication Data

US 2008/0138358 A1 Jun. 12, 2008

Related U.S. Application Data

(63) Continuation of application No. 10/382,479, filed on Mar. 6, 2003, now abandoned, which is a continuation of application No. 09/381,122, filed as application No. PCT/NL98/00146 on Mar. 11, 1998, now Pat. No. 6,551,594.

(30) Foreign Application Priority Data

Mar. 11, 1997 (EP) .................................. 97200730

(51) Int. Cl.
*A61K 39/00* (2006.01)
*C07K 4/00* (2006.01)
*C07K 14/00* (2006.01)
*C07H 21/02* (2006.01)
*C07H 21/04* (2006.01)
*C12P 21/04* (2006.01)

(52) U.S. Cl. ............... 424/265.1; 424/184.1; 424/191.1; 435/69.1; 435/69.5; 435/69.7; 530/300; 530/350; 536/23.1; 536/23.5; 536/23.7

(58) Field of Classification Search ....................... None
See application file for complete search history.

(56) References Cited

U.S. PATENT DOCUMENTS 6,551,594 B1  4/2003  van Milligen et al.

FOREIGN PATENT DOCUMENTS

CA            2215104            9/1996

(Continued)

OTHER PUBLICATIONS

Lederman et al (Molecular Immunology 28:1171-1181, 1991.*

(Continued)

*Primary Examiner*—Robert B Mondesi
*Assistant Examiner*—Padma V Baskar
(74) *Attorney, Agent, or Firm*—TraskBritt

(57) ABSTRACT

The invention relates to an ex vivo animal or challenge model as a method to identify protective (recombinant) proteins and rapidly measure protective immunity in intestinal segments directed against parasites and vaccines directed against parasitic infections. The invention further relates to vaccines directed against infection with parasites, such as *Fasciola hepatica*, which vaccines contain protective (recombinant) proteins identified and shown to be protective in studies using the ex vivo model. The invention further relates to protective (recombinant) proteins obtained from newly excysted juveniles (NEJ) of *Fasciola hepatica*. The protective (recombinant) protein corresponding to an NEJ protein has an apparent molecular weight of 32 kD and an N-terminal amino acid sequence comprising the sequence XXDVSWPFW-DRMYNY (SEQ ID NO:1).

9 Claims, 6 Drawing Sheets

FOREIGN PATENT DOCUMENTS

| | | |
|---|---|---|
| WO | WO 94/17820 | 8/1994 |
| WO | WO 96/29605 | 9/1996 |

OTHER PUBLICATIONS

Li et al, Proc. Natl. Acad. Sci. USA 77:3211-3214, 1980.*
Lammas et al 1982, pp. 52-56, ( The ELISA: enzyme-linked immunosorbent assay in veterinary research and Diagnosis, Edited by R. C. Wardley, J. R. Crowther, Martinu Nijhoff publishers under The Use of Elisa to Detect Antigen Release From Juvenile *Fasciola hepatica*).*
Mulcahy, G., Cathepsin L Proteinases as vaccines against infection with *Fasciola hepatica* (liver fluke) in ruminants, Research in Veterinary Science, 2001, pp. 83-86.
Berasain et al., J. Parasitol, 1997, 83; 1-5.
Bowie et al., Science, vol. 247: 1990; pp. 1306-1310.
Dalton et al., 1996, Infection and Immunity; 60; 5066-5074.
Herbert et al., The Dictionary of Immunology, Academic Press, 3rd Edition, London, 1985, pp. 58-59.
Houghten et al., Vaccines, 1986, edited by Fred Brown: Cold Spring Harbor Laboratory.
Illustrated Dictionary of Immunology 1995, CRC Press, Inc., edited by Julius M. Cruse, p. 21.
Kawano et al., J. Vet. Med. Sci. 1992; 54; 69-73.
Milner et al., 1994, sequence alignment.
Oshima et al., 1993, Journal of Protein chemistry, vol. 12, No. 4, pp. 403-412.
Saz Howard, 1981, Chapter 17, Medical Microbiology and Infectious Diseases, edited by Braude; W.B. Saunders Company, Philadelphia.
Tkalcevic et al., Biochemical and Biophysics Research Communications, 1995, 213; 169-174.
Wijffels et al., Biochem., 299; 781-790.
Cornelissen et al., Early immunodiagnosis of fasciolosis in ruminants using recominant *Fasciola hepatica* cathepsin L-like protease, International Journal of Parasitology, 2001, pp. 728-737, vol. 31.
Cornelissen et al., Use of a pre-selected epitope of cathepsin-L1 in a highly specific peptide-based immunoassay for the diagnosis of *Fasciola hepatica* infections in cattle, International Journal of Parasitology, 1999, pp. 685-696, vol. 29.
Gassenbeek et al., An experimental study of triclabendazole resistance of *Fasciola hepatica* in sheep, Veterinary Parasitology, 2001, pp. 37-43, vol. 95.
Harmsen et al., Identification of a novel *Fasciola hepatica* cathepsin L protease containing protective epitopes within the propeptide, International Journal for Parasitology, 2004, pp. 675-682, vol. 34.
Reszka et al., *Fasciola hepatica* procathepsin L3 protein expressed by a baculovirus recombinant can partly protect rats against fasciolosis, Vaccine, 2005, pp. 2987-2993, vol. 23.
Van Milligen et al., *Fasciola hepatica*: An Antigen Fraction Derived from Newly Excysted Juveniles, Containing an Immunoreactive 32-kDa Protein, Induces Strong Protective Immunity in Rats, Experimental Parasitology, 2000, pp. 163-171, vol. 94.
Van Milligen et al., Location of Induction and Expression of Protective Immunity against *Fasciola hepatica* at the Gut Level: A Study Using an Ex Vivo Infection Model with Ligated Gut Segments, J. Parasitol., 1998, pp. 771-777, vol. 84, No. 4.
Van Milligen et al., A novel ex vivo rat infection model to study protective immunity against *Fasciola hepatica* at the gut level, Journal of Immunological Methods, 1998, pp. 183-190, vol. 213.
Van Milligen et al., Protection against *Fasciola hepatica* in the intestine is highly correlated with eosinophil and immunoglobulin G1 responses against newly excysted juveniles, Parasite Immunology, 1999, pp. 243-251, vol. 21.
Van Milligen et al., Protection to *Fasciola hepatica* in the gut mucosa of immune rats is associated with infiltrates of eosinophils, IgG1 and IgG2a antibodies around the parasites, Parasite Immunology, 1998, pp. 285-292, vol. 20.
De Leeuw et al., Abstract, Comparison of three enzyme immunoassays for diagnosis of Dictyocaulus viviparus infection, Vet. Parasitol., Sep. 1993, pp. 229-241, vol. 49, No. 2-4.
Lang et al.; Host-Parasite Relationships of *Fasciola hepatica* in the White Mouse. VIII. Successful Vaccination with Culture Incubate Antigens and Antigens from Sonic Disruption of Immature Worms, The Journal of Parasitology, Dec. 1977, pp. 1046-1049, vol. 63, No. 6.

* cited by examiner

```
                    10              20              30              40
                     |               |               |               |
  1  T G G C A T C A G T G G A A G C G A A T G T A C A A T A A A G A A T A C A A T G   wijffelspro.seq
  1  T G G C A T C A G T G G A A G C G A A T G T A[T]A A T A A A G A A T A C A A[C]G   dal3pro.seq
  1  T G G C A T[G]A G T G G A A A[A]C G[G]A T G T A[T]A A T A A A G A[G]T A C A A T G   da210pro.seq
  1  T G G C A T[G]A[A]T G G A A G C G[G]A T G T A C A A[C]A A A G A A T A C A A T G   da211pro.seq 50              60              70              80
                     |               |               |               |
 41  G G G C T G A C G A T C A G C A C A G A C G A A A T A T T T G G G A A A A G A A   wijffelspro.seq
 41  G G G C T G A C G A T[G]A G C A C A G A C G A A A T A T T T G G G A A[G]A G A A   dal3pro.seq
 41  G[A]G C T G A C G A T[G]A G C A C A G[G]C G[G]A A[A]A T T T G G G A A[C]A G A A   da210pro.seq
 41  G[A]G[T]T G A C G A T[G C A]C A C A G A C G[G]A A T A T T T G G G A A[G]A G A A   da211pro.seq 90             100             110             120
                     |               |               |               |
 81  T G T G A A A C A T A T C C A A G A A C A T A A C C T A C G T C A C G A T C T C   wijffelspro.seq
 81  T G T G A A A C A T A T[T]C A A G A A C A[C]A A C C T A C G T C A C G A T C T C   dal3pro.seq
 81  T G T G A A A C A T A T C C A A G A A C A[C]A A C C T A C G T C A C G A T[A]T C   da210pro.seq
 81  T G T G A A A C A T A T C C A A G A A C A[C]A A C[A]T A C G T C A C G A T C T C   da211pro.seq 130             140             150             160
                     |               |               |               |
121  G G C C T C G T C A C C T A C A C A T T G G G A T T G A A C C A A T T C A C G G   wijffelspro.seq
121  G G C C T C G T C A C C T A C A C A T T G G G A T T G A A C C A A T T C A C[T]G   dal3pro.seq
121  G G C C T C G[C]C A C C T A C A C[G]T T G G G A T T G A A C C A A T T C A C[T]G   da210pro.seq
121  G G[A]C T C G T C A C[A]T A C A C[G]T T G G G A T T G A A[T]C A A T T C A C[T]G   da211pro.seq 170             180             190             200
                     |               |               |               |
161  A T A T G A C A T T C G A G G A A T T C A A G G C C A A A T A T C T A A C A G A   wijffelspro.seq
161  A T A T G A C A T T C G A G G A A T T C A A G G C C A A A T A T C T A A C A G A   dal3pro.seq
161  A[C C]T G A C[G]T T C G A G G A A T T C A A G G C C A A[G]T A T C T[G A]T A G A   da210pro.seq
161  A T A T G A C A T T C G A G G A A T T C A A G G C C A A A T A T C T A A[G]A G A   da211pro.seq 210             220             230             240
                     |               |               |               |
201  A A T G T C A C G C G C G T C C G A T A T A C T C T C A C A C G G T G T C C C G   wijffelspro.seq
201  A A T G[C]C A C G C G C G T C C G A T A T A C T C T C A C A C G G T[A]T C C C G   dal3pro.seq
201  A A T G T C A C[C G]A[A]G T C C G A[A T C]A C T C T C A[G]A C G G[C A]T[T G]C G   da210pro.seq
201  A A T[A C]C A C G C G C G T C C G A T A T A C[A]C T C A C A C G G[C A]T C C C G   da211pro.seq 250
                     |
241  T A T G A G G C G A A C A A T C G T                                               wijffelspro.seq
241  T A T G A G G C G A A C A A T C G T                                               dal3pro.seq
241  T A T G A G G C[C G]A[A G]A[C A A]T                                               da210pro.seq
241  T A T G A G G C[A]A A C[G]A T C G T                                               da211pro.seq
```

Figure 2A

```
                  10             20             30             40
1  W H Q W K R M Y N K E Y N G A D D Q H R R N I W E K N V K H I Q E H N L R H D L   Wijffels.pro
1  W H Q W K R M Y N K E Y N G A D D E H R R N I W E E N V K H I Q E H N L R H D L   da13pro.pro
1  W H E W K R M Y N K E Y N G A D D E H R R K I W E Q N V K H I Q E H N L R H D I   da210pro.pro
1  W H E W K R M Y N K E Y N G V D D A H R R N I W E E N V K H I Q E H N I R H D L   da211pro.pro 50             60             70             80
41 G L V T Y T L G L N Q F T D M T F E E F K A K Y L T E M S R A S D I L S H G V P   Wijffels.pro
41 G L V T Y T L G L N Q F T D M T F E E F K A K Y L T E M P R A S D I L S H G I P   da13pro.pro
41 G L A T Y T L G L N Q F T D L T F E E F K A K Y L I E M S P E S E S L S D G I A   da210pro.pro
41 G L V T Y T L G L N Q F T D M T F E E F K A K Y L R E I P R A S D I H S H G I P   da211pro.pro 81 Y E A N N R                                                                       Wijffels.pro
81 Y E A N N R                                                                       da13pro.pro
81 Y E A E D N                                                                       da210pro.pro
81 Y E A N D R                                                                       da211pro.pro
```

Figure 2B

```
         10           20           30          40
1  SN------DDLWHQWKRMYNKEYNGADDQHRRN-IWEKNV    F-hep.pro
1  QY------DDIWKQWKLKYNKTY-SDSNEIRRKAIFMRYV    S-man1.pro
1  QY------DEIWRQWKLKYNKTYTSNDDEMRRKMIFMRRI    S-jap.pro
1  TLTFDHSLEAQWTKWKAMHNRLY-GMNEEGWRAVWEKNM     H-sap.pro
1  ------NVDEKYVQFKLKYRKQYHETEDEIRFN-IFKSNI    S-man2.pro 50           60           70          80
34 KHIQEHNLRHDLGLVTYTLGLNQFTDMTEEFKAKYLTEM     F-hep.pro
34 EKIQQHNLRHDLGLEGYTMGLNQFCDMDWEEIKTIMLSKV    S-man1.pro
35 GKIQEHNLRHDLGLEGYTMGLNQFCDMEWEEVNRIMFPKV    S-jap.pro
40 KMIELHNQEYREGKHSFTMAMNAFGDMTSEEFRQVM--NG    H-sap.pro
34 LKAQLYQV-FVRGSAIY--GVTPYSDLTTDEFARTHLTAS    S-man2.pro 90
74 SRASDILSH-GVPYEANNR    F-hep.pro
74 FGNSPLWDDKKEELELSND    S-man1.pro
75 FGNSPLWNDGNELELTNK     S-jap.pro
78 FQNRKPRKGKVFQEPLFYE    H-sap.pro
71 WVVPSSRSNTPTSLGKEVN    S-man2.pro
```

Figure 3

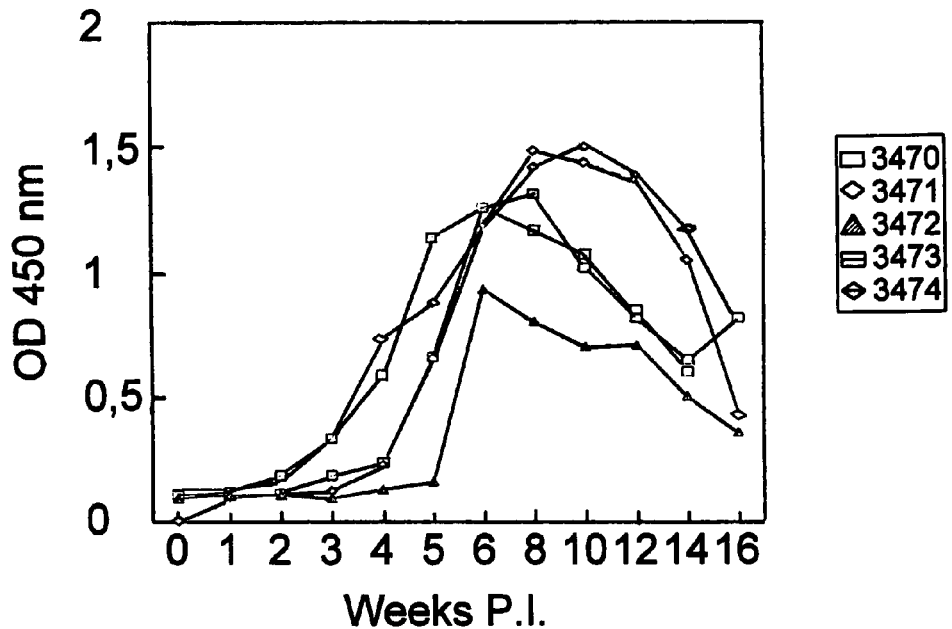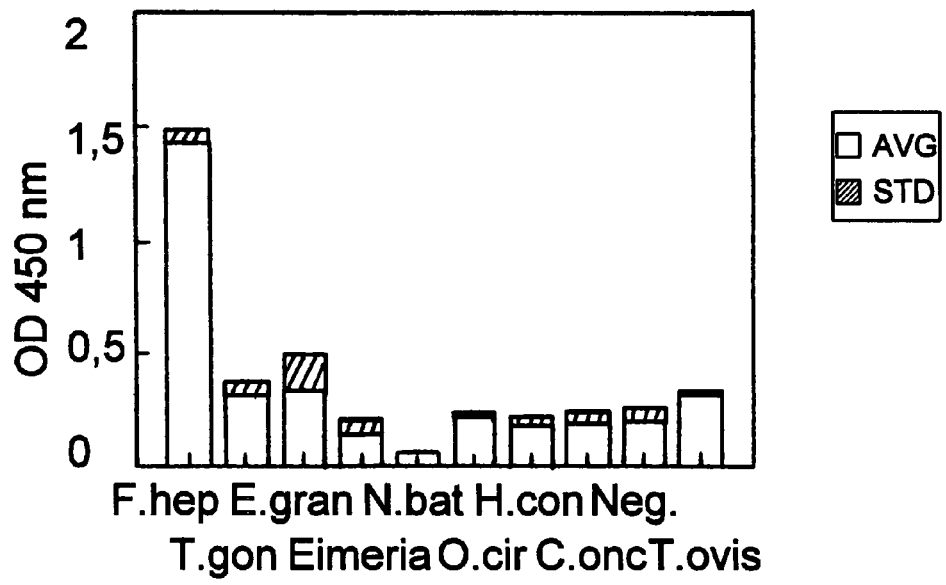
Figure 5

SEQUENCE LISTING

```
<160> NUMBER OF SEQ ID NOS: 32

<210> SEQ ID NO 1
<211> LENGTH: 15
<212> TYPE: PRT
<213> ORGANISM: Fasciola hepatica
<220> FEATURE:
<221> NAME/KEY: PEPTIDE
<222> LOCATION: (1)..(15)
<223> OTHER INFORMATION: /Note="N-terminal amino acid sequence of
      protective protein, whereby Xaa can be any Amino Acid"

<400> SEQUENCE: 1

Xaa Xaa Asp Val Ser Trp Pro Phe Trp Asp Arg Met Tyr Asn Tyr
 1               5                  10                  15

<210> SEQ ID NO 2
<211> LENGTH: 19
<212> TYPE: PRT
<213> ORGANISM: Fasciola hepatica
<220> FEATURE:
<221> NAME/KEY: PEPTIDE
<222> LOCATION: (1)..(19)
<223> OTHER INFORMATION: /Note="immunogenic determinant, pos. 15-33"

<400> SEQUENCE: 2

Gly Ser Asn Asp Asp Leu Trp His Gln Trp Lys Arg Met Tyr Asn Lys
 1               5                  10                  15

Glu Tyr Asn

<210> SEQ ID NO 3
<211> LENGTH: 18
<212> TYPE: PRT
<213> ORGANISM: Fasciola hepatica
<220> FEATURE:
<221> NAME/KEY: PEPTIDE
<222> LOCATION: (1)..(18)
<223> OTHER INFORMATION: /Note="immunogenic determinant, pos.25-42"
```

-continued

```
<400> SEQUENCE: 3

Lys Arg Met Tyr Asn Lys Glu Tyr Asn Gly Ala Asp Asp Gln His Arg
 1               5                  10                  15

Arg Asn

<210> SEQ ID NO 4
<211> LENGTH: 20
<212> TYPE: PRT
<213> ORGANISM: Fasciola hepatica
<220> FEATURE:
<221> NAME/KEY: PEPTIDE
<222> LOCATION: (1)..(20)
<223> OTHER INFORMATION: /Note="immunogenic determinant, pos. 103-122"

<400> SEQUENCE: 4

Ala Asn Asn Arg Ala Val Pro Asp Lys Ile Asp Trp Arg Glu Ser Gly
 1               5                  10                  15

Tyr Val Thr Glu
            20

<210> SEQ ID NO 5
<211> LENGTH: 20
<212> TYPE: PRT
<213> ORGANISM: Fasciola hepatica
<220> FEATURE:
<221> NAME/KEY: PEPTIDE
<222> LOCATION: (1)..(20)
<223> OTHER INFORMATION: /Note="immunogenic determinant, pos. 110-129"

<400> SEQUENCE: 5

Asp Lys Ile Asp Trp Arg Glu Ser Gly Tyr Val Thr Glu Val Lys Asp
 1               5                  10                  15

Gln Gly Asn Cys
            20

<210> SEQ ID NO 6
<211> LENGTH: 16
<212> TYPE: PRT
<213> ORGANISM: Fasciola hepatica
<220> FEATURE:
<221> NAME/KEY: PEPTIDE
<222> LOCATION: (1)..(16)
<223> OTHER INFORMATION: /Note="immunogenic determinant, pos. 296-311"

<400> SEQUENCE: 6

Gly Glu Arg Gly Tyr Ile Arg Met Ala Arg Asn Arg Gly Asn Met Cys
 1               5                  10                  15

<210> SEQ ID NO 7
<211> LENGTH: 21
<212> TYPE: DNA
<213> ORGANISM: Fasciola hepatica
<220> FEATURE:
<221> NAME/KEY: primer_bind
<222> LOCATION: (1)..(21)
<223> OTHER INFORMATION: /Note="primer forward"

<400> SEQUENCE: 7
tggcatcagt ggaagcgaat g                                        21

<210> SEQ ID NO 8
<211> LENGTH: 21
<212> TYPE: DNA
<213> ORGANISM: Fasciola hepatica
<220> FEATURE:
<221> NAME/KEY: primer_bind
```

```
<222> LOCATION: (1)..(21)
<223> OTHER INFORMATION: /Note="primer reversed"

<400> SEQUENCE: 8
ataaccagat tcacgccagt c                                        21

<210> SEQ ID NO 9
<211> LENGTH: 21
<212> TYPE: DNA
<213> ORGANISM: Fasciola hepatica
<220> FEATURE:
<221> NAME/KEY: primer_bind
<222> LOCATION: (1)..(21)
<223> OTHER INFORMATION: /Note="primer forward, whereby N stands for any
      nucleotide A or C"

<400> SEQUENCE: 9
tggcaygart ggaarmgnat g                                        21

<210> SEQ ID NO 10
<211> LENGTH: 21
<212> TYPE: DNA
<213> ORGANISM: Fasciola hepatica
<220> FEATURE:
<221> NAME/KEY: primer_bind
<222> LOCATION: (1)..(21)
<223> OTHER INFORMATION: /Note="primer reversed, whereby N stands for
      any nucleotide A or C"

<400> SEQUENCE: 10
rtanccrtay tcnckccart c                                        21

<210> SEQ ID NO 11
<211> LENGTH: 21
<212> TYPE: DNA
<213> ORGANISM: Fasciola hepatica
<220> FEATURE:
<221> NAME/KEY: primer_bind
<222> LOCATION: (1)..(21)
<223> OTHER INFORMATION: /Note="primer forward, whereby N stands for any
      nucleotide A or C"

<400> SEQUENCE: 11
tgcccnttyt ggaarmgnat g                                        21

<210> SEQ ID NO 12
<211> LENGTH: 18
<212> TYPE: DNA
<213> ORGANISM: Fasciola hepatica
<220> FEATURE:
<221> NAME/KEY: primer_bind
<222> LOCATION: (1)..(18)
<223> OTHER INFORMATION: /Note="primer forward NEJ, pos. 398-471"

<400> SEQUENCE: 12
atcagggaca atggttcc                                            18

<210> SEQ ID NO 13
<211> LENGTH: 21
<212> TYPE: DNA
<213> ORGANISM: Fasciola hepatica
<220> FEATURE:
<221> NAME/KEY: primer_bind
<222> LOCATION: (1)..(21)
<223> OTHER INFORMATION: /Note="primer reversed NEJ, pos. 752-772"

<400> SEQUENCE: 13
gaagtcagat tgagcatcca c                                        21
```

```
<210> SEQ ID NO 14
<211> LENGTH: 20
<212> TYPE: DNA
<213> ORGANISM: Fasciola hepatica
<220> FEATURE:
<221> NAME/KEY: primer_bind
<222> LOCATION: (1)..(20)
<223> OTHER INFORMATION: /Note="primer forward NEJ, pos. 638-657"

<400> SEQUENCE: 14
caatacagga aagagcttgg                                              20

<210> SEQ ID NO 15
<211> LENGTH: 19
<212> TYPE: DNA
<213> ORGANISM: Fasciola hepatica
<220> FEATURE:
<221> NAME/KEY: primer_bind
<222> LOCATION: ()..()
<223> OTHER INFORMATION: /Note="primer forward Adult, pos. 407-425"

<400> SEQUENCE: 15
actgtggttc ctgttgggc                                               19

<210> SEQ ID NO 16
<211> LENGTH: 22
<212> TYPE: DNA
<213> ORGANISM: Fasciola hepatica
<220> FEATURE:
<221> NAME/KEY: primer_bind
<222> LOCATION: (1)..(22)
<223> OTHER INFORMATION: /Note="primer reversed Adult, pos. 779-800"

<400> SEQUENCE: 16
ctctgaataa ataccactcc tg                                           22

<210> SEQ ID NO 17
<211> LENGTH: 12
<212> TYPE: PRT
<213> ORGANISM: Fasciola hepatica
<220> FEATURE:
<221> NAME/KEY: PEPTIDE
<222> LOCATION: (1)..(12)
<223> OTHER INFORMATION: /Note="N-terminal amino acid sequence of
      protective protein, whereby Xaa can be any Amino Acid"

<400> SEQUENCE: 17

Xaa Xaa Trp Ala Val Leu Val Ala Gly Gly Ser Asp
 1               5                  10

<210> SEQ ID NO 18
<211> LENGTH: 20
<212> TYPE: PRT
<213> ORGANISM: Fasciola hepatica
<220> FEATURE:
<221> NAME/KEY: PEPTIDE
<222> LOCATION: (1)..(20)
<223> OTHER INFORMATION: /Note="N-terminal amino acid sequence of
      protective protein"

<400> SEQUENCE: 18

Asp Val Pro Ala Ser Ile Asp Trp Arg Gln Tyr Gly Tyr Val Thr Glu
 1               5                  10                  15

Val Lys Asp Gln
            20
```

```
<210> SEQ ID NO 19
<211> LENGTH: 258
<212> TYPE: DNA
<213> ORGANISM: Fasciola hepatica
<220> FEATURE:
<221> NAME/KEY: CDS
<222> LOCATION: (1)..(258)
<223> OTHER INFORMATION: /Note="nucleic acid sequence as cathepsin L
      proregion"

<400> SEQUENCE: 19 tgg cat cag tgg aag cga atg tac aat aaa gaa tac aat ggg gct gac      48
Trp His Gln Trp Lys Arg Met Tyr Asn Lys Glu Tyr Asn Gly Ala Asp
 1               5                  10                  15 gat cag cac aga cga aat att tgg gaa aag aat gtg aaa cat atc caa      96
Asp Gln His Arg Arg Asn Ile Trp Glu Lys Asn Val Lys His Ile Gln
             20                  25                  30 gaa cat aac cta cgt cac gat ctc ggc ctc gtc acc tac aca ttg gga     144
Glu His Asn Leu Arg His Asp Leu Gly Leu Val Thr Tyr Thr Leu Gly
         35                  40                  45 ttg aac caa ttc acg gat atg aca ttc gag gaa ttc aag gcc aaa tat     192
Leu Asn Gln Phe Thr Asp Met Thr Phe Glu Glu Phe Lys Ala Lys Tyr
     50                  55                  60 cta aca gaa atg tca cgc gcg tcc gat ata ctc tca cac ggt gtc ccg     240
Leu Thr Glu Met Ser Arg Ala Ser Asp Ile Leu Ser His Gly Val Pro
 65                  70                  75                  80 tat gag gcg aac aat cgt                                             258
Tyr Glu Ala Asn Asn Arg
                 85

<210> SEQ ID NO 20
<211> LENGTH: 86
<212> TYPE: PRT
<213> ORGANISM: Fasciola hepatica

<400> SEQUENCE: 20

Trp His Gln Trp Lys Arg Met Tyr Asn Lys Glu Tyr Asn Gly Ala Asp
 1               5                  10                  15

Asp Gln His Arg Arg Asn Ile Trp Glu Lys Asn Val Lys His Ile Gln
             20                  25                  30

Glu His Asn Leu Arg His Asp Leu Gly Leu Val Thr Tyr Thr Leu Gly
         35                  40                  45

Leu Asn Gln Phe Thr Asp Met Thr Phe Glu Glu Phe Lys Ala Lys Tyr
     50                  55                  60

Leu Thr Glu Met Ser Arg Ala Ser Asp Ile Leu Ser His Gly Val Pro
 65                  70                  75                  80

Tyr Glu Ala Asn Asn Arg
                 85

<210> SEQ ID NO 21
<211> LENGTH: 258
<212> TYPE: DNA
<213> ORGANISM: Fasciola hepatica
<220> FEATURE:
<221> NAME/KEY: CDS
<222> LOCATION: (1)..(258)
<223> OTHER INFORMATION: /Note="nucleic acid sequence as cathepsin L
      proregion"

<400> SEQUENCE: 21 tgg cat cag tgg aag cga atg tat aat aaa gaa tac aac ggg gct gac      48
Trp His Gln Trp Lys Arg Met Tyr Asn Lys Glu Tyr Asn Gly Ala Asp
 1               5                  10                  15
```

```
gat gag cac aga cga aat att tgg gaa gag aat gtg aaa cat att caa      96
Asp Glu His Arg Arg Asn Ile Trp Glu Glu Asn Val Lys His Ile Gln
             20                  25                  30 gaa cac aac cta cgt cac gat ctc ggc ctc gtc acc tac aca ttg gga     144
Glu His Asn Leu Arg His Asp Leu Gly Leu Val Thr Tyr Thr Leu Gly
         35                  40                  45 ttg aac caa ttc act gat atg aca ttc gag gaa ttc aag gcc aaa tat     192
Leu Asn Gln Phe Thr Asp Met Thr Phe Glu Glu Phe Lys Ala Lys Tyr
     50                  55                  60 cta aca gaa atg cca cgc gcg tcc gat ata ctc tca cac ggt atc ccg     240
Leu Thr Glu Met Pro Arg Ala Ser Asp Ile Leu Ser His Gly Ile Pro
 65                  70                  75                  80 tat gag gcg aac aat cgt                                             258
Tyr Glu Ala Asn Asn Arg
                 85

<210> SEQ ID NO 22
<211> LENGTH: 86
<212> TYPE: PRT
<213> ORGANISM: Fasciola hepatica

<400> SEQUENCE: 22

Trp His Gln Trp Lys Arg Met Tyr Asn Lys Glu Tyr Asn Gly Ala Asp
 1               5                  10                  15

Asp Glu His Arg Arg Asn Ile Trp Glu Glu Asn Val Lys His Ile Gln
             20                  25                  30

Glu His Asn Leu Arg His Asp Leu Gly Leu Val Thr Tyr Thr Leu Gly
         35                  40                  45

Leu Asn Gln Phe Thr Asp Met Thr Phe Glu Glu Phe Lys Ala Lys Tyr
     50                  55                  60

Leu Thr Glu Met Pro Arg Ala Ser Asp Ile Leu Ser His Gly Ile Pro
 65                  70                  75                  80

Tyr Glu Ala Asn Asn Arg
                 85

<210> SEQ ID NO 23
<211> LENGTH: 258
<212> TYPE: DNA
<213> ORGANISM: Fasciola hepatica
<220> FEATURE:
<221> NAME/KEY: CDS
<222> LOCATION: (1)..(258)
<223> OTHER INFORMATION: /Note="nucleic acid sequence as cathepsin L
      proregion"

<400> SEQUENCE: 23 tgg cat gag tgg aaa cgg atg tat aat aaa gag tac aat gga gct gac      48
Trp His Glu Trp Lys Arg Met Tyr Asn Lys Glu Tyr Asn Gly Ala Asp
 1               5                  10                  15 gat gag cac agg cgg aaa att tgg gaa cag aat gtg aaa cat atc caa      96
Asp Glu His Arg Arg Lys Ile Trp Glu Gln Asn Val Lys His Ile Gln
             20                  25                  30 gaa cac aac cta cgt cac gat atc ggc ctc gcc acc tac acg ttg gga     144
Glu His Asn Leu Arg His Asp Ile Gly Leu Ala Thr Tyr Thr Leu Gly
         35                  40                  45 ttg aac caa ttc act gac ctg acg ttc gag gaa ttc aag gcc aag tat     192
Leu Asn Gln Phe Thr Asp Leu Thr Phe Glu Glu Phe Lys Ala Lys Tyr
     50                  55                  60 ctg ata gaa atg tca ccg gag tcc gaa tca ctc tca gac ggt att gcg     240
Leu Ile Glu Met Ser Pro Glu Ser Glu Ser Leu Ser Asp Gly Ile Ala
 65                  70                  75                  80
```

```
tat gag gcc gaa gac aat                                              258
Tyr Glu Ala Glu Asp Asn
            85

<210> SEQ ID NO 24
<211> LENGTH: 86
<212> TYPE: PRT
<213> ORGANISM: Fasciola hepatica

<400> SEQUENCE: 24

Trp His Glu Trp Lys Arg Met Tyr Asn Lys Glu Tyr Asn Gly Ala Asp
1               5                   10                  15

Asp Glu His Arg Arg Lys Ile Trp Glu Gln Asn Val Lys His Ile Gln
            20                  25                  30

Glu His Asn Leu Arg His Asp Ile Gly Leu Ala Thr Tyr Thr Leu Gly
        35                  40                  45

Leu Asn Gln Phe Thr Asp Leu Thr Phe Glu Glu Phe Lys Ala Lys Tyr
    50                  55                  60

Leu Ile Glu Met Ser Pro Glu Ser Glu Ser Leu Ser Asp Gly Ile Ala
65                  70                  75                  80

Tyr Glu Ala Glu Asp Asn
            85

<210> SEQ ID NO 25
<211> LENGTH: 258
<212> TYPE: DNA
<213> ORGANISM: Fasciola hepatica
<220> FEATURE:
<221> NAME/KEY: CDS
<222> LOCATION: (1)..(258)
<223> OTHER INFORMATION: /Note="nucleic acid sequence as cathepsin L
      proregion"

<400> SEQUENCE: 25 tgg cat gaa tgg aag cgg atg tac aac aaa gaa tac aat gga gtt gac    48
Trp His Glu Trp Lys Arg Met Tyr Asn Lys Glu Tyr Asn Gly Val Asp
1               5                   10                  15 gat gca cac aga cgg aat att tgg gaa gag aat gtg aaa cat atc caa    96
Asp Ala His Arg Arg Asn Ile Trp Glu Glu Asn Val Lys His Ile Gln
            20                  25                  30 gaa cac aac ata cgt cac gat ctc gga ctc gtc aca tac acg ttg gga  144
Glu His Asn Ile Arg His Asp Leu Gly Leu Val Thr Tyr Thr Leu Gly
        35                  40                  45 ttg aat caa ttc act gat atg aca ttc gag gaa ttc aag gcc aaa tat  192
Leu Asn Gln Phe Thr Asp Met Thr Phe Glu Glu Phe Lys Ala Lys Tyr
    50                  55                  60 cta aga gaa ata cca cgc gcg tcc gat ata cac tca cac ggc atc ccg  240
Leu Arg Glu Ile Pro Arg Ala Ser Asp Ile His Ser His Gly Ile Pro
65                  70                  75                  80 tat gag gca aac gat cgt                                            258
Tyr Glu Ala Asn Asp Arg
            85

<210> SEQ ID NO 26
<211> LENGTH: 86
<212> TYPE: PRT
<213> ORGANISM: Fasciola hepatica

<400> SEQUENCE: 26

Trp His Glu Trp Lys Arg Met Tyr Asn Lys Glu Tyr Asn Gly Val Asp
1               5                   10                  15

Asp Ala His Arg Arg Asn Ile Trp Glu Glu Asn Val Lys His Ile Gln
            20                  25                  30
```

-continued

```
                    20                  25                  30

Glu His Asn Ile Arg His Asp Leu Gly Leu Val Thr Tyr Thr Leu Gly
            35                  40                  45

Leu Asn Gln Phe Thr Asp Met Thr Phe Glu Glu Phe Lys Ala Lys Tyr
        50                  55                  60

Leu Arg Glu Ile Pro Arg Ala Ser Asp Ile His Ser His Gly Ile Pro
 65                  70                  75                  80

Tyr Glu Ala Asn Asp Arg
                85

<210> SEQ ID NO 27
<211> LENGTH: 91
<212> TYPE: PRT
<213> ORGANISM: Fasciola hepatica
<220> FEATURE:
<221> NAME/KEY: CHAIN
<222> LOCATION: (1)..(91)
<223> OTHER INFORMATION: /Note="cathepsin L proregion"

<400> SEQUENCE: 27

Ser Asn Asp Asp Leu Trp His Gln Trp Lys Arg Met Tyr Asn Lys Glu
 1               5                  10                  15

Tyr Asn Gly Ala Asp Asp Gln His Arg Arg Asn Ile Trp Glu Lys Asn
            20                  25                  30

Val Lys His Ile Gln Glu His Asn Leu Arg His Asp Leu Gly Leu Val
        35                  40                  45

Thr Tyr Thr Leu Gly Leu Asn Gln Phe Thr Asp Met Thr Phe Glu Glu
    50                  55                  60

Phe Lys Ala Lys Tyr Leu Thr Glu Met Ser Arg Ala Ser Asp Ile Leu
 65                  70                  75                  80

Ser His Gly Val Pro Tyr Glu Ala Asn Asn Arg
                85                  90

<210> SEQ ID NO 28
<211> LENGTH: 92
<212> TYPE: PRT
<213> ORGANISM: Fasciola hepatica
<220> FEATURE:
<221> NAME/KEY: CHAIN
<222> LOCATION: (1)..(92)
<223> OTHER INFORMATION: /Note="cathepsin L proregion"

<400> SEQUENCE: 28

Gln Tyr Asp Asp Ile Trp Lys Gln Trp Lys Leu Lys Tyr Asn Lys Thr
 1               5                  10                  15

Tyr Ser Asp Ser Asn Glu Ile Arg Arg Lys Ala Ile Phe Met Arg Tyr
            20                  25                  30

Val Glu Lys Ile Gln Gln His Asn Leu Arg His Asp Leu Gly Leu Glu
        35                  40                  45

Gly Tyr Thr Met Gly Leu Asn Gln Phe Cys Asp Met Asp Trp Glu Glu
    50                  55                  60

Ile Lys Thr Ile Met Leu Ser Lys Val Phe Gly Asn Ser Pro Leu Trp
 65                  70                  75                  80

Asp Asp Lys Lys Glu Glu Leu Glu Leu Ser Asn Asp
                85                  90

<210> SEQ ID NO 29
<211> LENGTH: 93
<212> TYPE: PRT
<213> ORGANISM: Fasciola hepatica
```

```
<220> FEATURE:
<221> NAME/KEY: CHAIN
<222> LOCATION: (1)..(93)
<223> OTHER INFORMATION: /Note="cathepsin L proregion"

<400> SEQUENCE: 29

Gln Tyr Asp Glu Ile Trp Arg Gln Trp Lys Leu Lys Tyr Asn Lys Thr
  1               5                  10                  15

Tyr Thr Ser Asn Asp Asp Glu Met Arg Arg Lys Met Ile Phe Met Arg
             20                  25                  30

Arg Ile Gly Lys Ile Gln Glu His Asn Leu Arg His Asp Leu Gly Leu
         35                  40                  45

Glu Gly Tyr Thr Met Gly Leu Asn Gln Phe Cys Asp Met Glu Trp Glu
 50                  55                  60

Glu Val Asn Arg Ile Met Phe Pro Lys Val Phe Gly Asn Ser Pro Leu
 65                  70                  75                  80

Trp Asn Asp Asp Gly Asn Glu Leu Glu Leu Thr Asn Lys
                 85                  90

<210> SEQ ID NO 30
<211> LENGTH: 96
<212> TYPE: PRT
<213> ORGANISM: Fasciola hepatica
<220> FEATURE:
<221> NAME/KEY: CHAIN
<222> LOCATION: (1)..(96)
<223> OTHER INFORMATION: /Note="cathepsin L proregion"

<400> SEQUENCE: 30

Thr Leu Thr Phe Asp His Ser Leu Glu Ala Gln Trp Thr Lys Trp Lys
  1               5                  10                  15

Ala Met His Asn Arg Leu Tyr Gly Met Asn Glu Glu Gly Trp Arg Arg
             20                  25                  30

Ala Val Trp Glu Lys Asn Met Lys Met Ile Glu Leu His Asn Gln Glu
         35                  40                  45

Tyr Arg Glu Gly Lys His Ser Phe Thr Met Ala Met Asn Ala Phe Gly
 50                  55                  60

Asp Met Thr Ser Glu Glu Phe Arg Gln Val Met Asn Gly Phe Gln Asn
 65                  70                  75                  80

Arg Lys Pro Arg Lys Gly Lys Val Phe Gln Glu Pro Leu Phe Tyr Glu
                 85                  90                  95

<210> SEQ ID NO 31
<211> LENGTH: 89
<212> TYPE: PRT
<213> ORGANISM: Fasciola hepatica
<220> FEATURE:
<221> NAME/KEY: CHAIN
<222> LOCATION: (1)..(89)
<223> OTHER INFORMATION: /Note="cathepsin L proregion"

<400> SEQUENCE: 31

Asn Val Asp Glu Lys Tyr Val Gln Phe Lys Leu Lys Tyr Arg Lys Gln
  1               5                  10                  15

Tyr His Glu Thr Glu Asp Glu Ile Arg Phe Asn Ile Phe Lys Ser Asn
             20                  25                  30

Ile Leu Lys Ala Gln Leu Tyr Gln Val Phe Val Arg Gly Ser Ala Ile
         35                  40                  45

Tyr Gly Val Thr Pro Tyr Ser Asp Leu Thr Thr Asp Glu Phe Ala Arg
 50                  55                  60
```

-continued

```
Thr His Leu Thr Ala Ser Trp Val Val Pro Ser Ser Arg Ser Asn Thr
65                  70                  75                  80

Pro Thr Ser Leu Gly Lys Glu Val Asn
                85

<210> SEQ ID NO 32
<211> LENGTH: 15
<212> TYPE: PRT
<213> ORGANISM: Fasciola hepatica
<220> FEATURE:
<221> NAME/KEY: PEPTIDE
<222> LOCATION: (1)..(15)
<223> OTHER INFORMATION: Peptide

<400> SEQUENCE: 32

Ala Val Pro Asp Lys Ile Asp Trp Arg Glu Gln Gly Tyr Val Thr
1               5                   10                  15
```

EX VIVO ANIMAL OR CHALLENGE MODEL AS METHOD TO MEASURE PROTECTIVE IMMUNITY DIRECTED AGAINST PARASITES AND VACCINES SHOWN TO BE PROTECTIVE IN THE METHOD

CROSS-REFERENCE TO RELATED APPLICATION

This application is a continuation of U.S. patent application Ser. No. 10/382,479, filed Mar. 6, 2003 now abandoned, which is a continuation of U.S. patent application Ser. No. 09/381,122, filed Dec. 23, 1999, now U.S. Pat. No. 6,551,594, issued Apr. 22, 2003, which claims priority from PCT Patent Application No. PCT/NL98/00146, filed Mar. 11, 1998, and published, in English, on Sep. 17, 1998, as WO 98/40497, the entire contents of each of which are incorporated herein by this reference.

BACKGROUND OF THE INVENTION

1. Field of the Invention

This invention relates to biotechnology generally and, more specifically, to an ex vivo animal or challenge model as a method to measure protective circuitry directed against parasites and vaccines shown to be protective in the method.

2. State of the Art

Only a few vaccines against parasites are commercially available. Most of these vaccines are based on attenuated live parasites that induce natural, protective immunity and cause less severe pathological damage. These parasite vaccines include one directed against *Dictyocaulus viviparus* (e.g., Dictol, Glaxo), undoubtedly the most successful anti-parasite vaccine, and analogous therewith a vaccine against *Dictyocaulus filaria*, the lung worm in sheep (Sharma et al. 1988). These vaccines are based on live but irradiated third-stage larvae (Peacock and Pointer 1980). Another attenuated vaccine is directed against the hookworm *Ancylostoma caninum* in dogs. However, this vaccine has been marketed only for a short time in the USA; marketing was discontinued because the American veterinary profession did not accept this live vaccine (Urquhart 1980). An attenuated vaccine against *Babesia bovis* has been in use for nearly a century in Australia (Purnell 1980) and a dead vaccine based on metabolic products named "Pirodog" is used to vaccinate dogs against *B. canis* (Moreau 1986).

Vaccination trials in sheep with a recombinant vaccine against the tape worm *Taenia ovis* (Johnson et al. 1989) and the concealed antigen H11 from *Haemonchus contortus* (Newton 1995, review) have been performed successfully. A trial with the SPf66 malaria vaccine in Africa has recently been completed. The efficiency against clinical malaria in areas of high transmission was 31% and the product appeared to be safe. However, because it is not fully understood how SPf66 mediates protection, the development of improved vaccines is hampered (Tanner et al. 1995, review).

Problems of developing anti-parasite vaccines are abundant. Parasites have complex life cycles and each stage expresses different sets of antigens. Moreover, the different stages are often associated with different sites in the body. For most parasites little is known about the immune mechanisms involved in natural immunity and about the stage of the parasite inducing this immunity.

Most often, no reproducible animal model is available to study these mechanisms, thereby blocking a new approach in vaccine development. As mentioned above, most available vaccines are based on attenuated live parasites. These vaccines can sometimes be successful because the "vaccine parasites" follow the correct route of infection and deliver a wide array of stage-specific antigens. However, such vaccines must challenge the acceptance of the public (e.g., *Ancylostoma caninum* vaccine), especially when they are for human use (e.g., *Schistosoma mansoni* vaccine, Taylor et al. 1986). Moreover, live vaccines, in general, have a short shelf-life and are relatively expensive. From this perspective there is an obvious need for vaccines that are based on (recombinant) proteins derived from the parasite. However, the identification of such protective proteins meets a great number of difficulties, as shown below as an example for *Fasciola hepatica*.

The trematode parasite *Fasciola hepatica* mainly infects cattle and sheep. Sometimes also humans get infected. The parasite causes considerable economic losses in, for example, western Europe, Australia and South America. The metacercariae of *Fasciola hepatica* enter its host by the oral route, penetrate the gut wall within four to seven hours (Dawes 1963; Burden et al. 1981; Burden et al. 1983; Kawano et al. 1992) and migrate through the peritoneal cavity towards the target organ, the liver. Oral infection of cattle results in almost complete protection against a challenge, whereas sheep often die from an infection and do not acquire natural immunity. Both the natural host (cattle) and the animal model (rat) acquire natural immunity after infection (Doy and Hughes 1984; Hayes, Bailer and Mitrovic 1973). Therefore, rats are often used to study resistance in cattle. In the rat a large part of natural immunity is expressed in the gut mucosa, the porte d'entree of the parasite. In immune rats, about 80% of the challenge newly excysted juvenile stages (NEJs) is eliminated in the route from the gut lumen to the peritoneal cavity (Hayes and Mitrovic 1977; Rajasekariah and Howell 1977; Doy, Hughes and Harness 1978/1981; Doy and Hughes 1982; Burden et al. 1981/1983). Based on natural immunity, a vaccine based on irradiated *Fasciola gigantica* metacercariae was developed for cattle (Bitakaramire 1973). In the seventies and eighties many vaccination experiments have been performed with antigen extracts of adult and juvenile flukes (Haroun and Hillyer 1980, review). However, these studies lead to conflicting or disputable results. For example, subcutaneous or intramuscular injection of rats with adult or juvenile fluke extracts did not result in protection (Oldham and Hughes 1982; Burden et al. 1982; Oldham 1983). Adult fluke extracts given intraperitoneally in Freund complete adjuvant (FCA) or incomplete Freund adjuvant (IFA) resulted in about 50% protection (Oldham and Hughes 1982; Oldham 1983). Using very high antigen doses of *Bordetella pertussis* as additional adjuvant this protection reached 80% to 86% (Oldham and Hughes 1982; Oldham 1983). Extracts of four-week-old juveniles given intraperitoneally in $AlOH_3$ did not induce protection in the studies of Pfister et al. (1984/85), whereas 16-day old juvenile extracts provided 86% protection in mice, without the use of adjuvant (Lang and Hall 1977). Subcutaneous sensitization of cattle with sonicated 16-day-old juveniles resulted in more than 90% protection (Hall and Lang 1978). Intramuscular injection of calves with an isolated fraction from adult *Fasciola hepatica* ($Fh_{SmIII}$), with an immunogenic 12 kD protein as major component, resulted in 55% protection (Hillyer et al. 1987).

Since 1990, several *Fasciola hepatica* vaccine candidate antigens have been isolated and/or produced. Most of these antigens are derived from adult flukes and share homology with *Schistosoma mansoni* antigens. Glutathion S-transferases (GST) are enzymes amongst others active in the cellular detoxification system. Immunization of sheep (n=9) with GST purified from adult *Fasciola hepatica*, injected s.c.

in FCA, with a boost immunization 4 weeks later in IFA, resulted in 57% protection (Sexton et al. 1990). Immunization of rats with GST provided no protection (Howell et al. 1988). Vaccination trials in cattle performed by Ciba Animal Health Research (Switzerland) and The Victorian Institute of Animal Science (Australia), resulted in 49% to 69% protection (Morrison et al. 1996).

Intradermal/subcutaneous immunization with recombinant *S. mansoni* fatty acid-binding protein Sm14 in FCA, provided complete protection against *Fasciola hepatica* challenge in mice (Tendler et al. 1996). PCT International Patent Publication WO 94/09142 suggests the use of proteases having cathepsin L type activity, derived of *Fasciola hepatica*, in the formulation of vaccines for combating helminth parasites; immunization of rabbits with the purified mature enzyme resulted in rabbit antibodies capable of decreasing the activity of the enzyme in vitro.

However, levels of protection obtained with *F. hepatica* cathepsin L or hemoglobin in cattle were only 53.7% or 43.5%, respectively (Dalton et al. 1996). Cathepsin L belongs to a family of cysteine proteinases, secreted by all stages of the developing parasite. Cathepsin L from *F. hepatica* is most active at slightly acid or neutral pH (Dalton and Heffernan, 1989). The functions of this proteinase include disruption of host immune function by cleaving host immunoglobulin in a papain-like manner (Smith et al. 1993) and preventing antibody mediated attachment of immune effector cells to the parasite (Carmona et al. 1993). Moreover, cathepsin L is capable of degradation of extracellular matrix and basement membrane components (Berasain et al. 1997), and prepares mucosal surface to be penetrated by a parasite indicating that cathepsin L is involved in tissue invasion. Because of its crucial biological functions, cathepsin L proteases are considered important candidates for the development of an antiparasite vaccine.

Cathepsin L is synthesized as a preprotein with a 15-amino-acid ("aa")-long peptide presequence, a 91-aa-long peptide prosequence or proregion and a 220-aa-long poly)peptide enzymatic part. Of cysteine proteinases the preregion is removed immediately after synthesis and the proprotein comprising the proregion and the part that (constitutes the mature enzyme) is transported to the Golgi. Conversion to the mature enzyme and thus conversion to an enzymatically active state, occurs in the lysosomes and could be due to cathepsin D or to autoactivation. In some cases precursors containing the proregion are secreted (North et al. 1990). Cathepsin L itself has a high affinity for a substrate with Arg at the P1 position and a hydrophobic residue (Phe) at the P2 position (Dowd et al. 1994). It also has autocatalytic activity and cleaves off its prosequence before it obtains its mature enzymatic activity. Cathepsin L2 also cleaves peptides containing Pro at the P2 position, and is therefore capable of cleaving fibrinogen and producing a fibrin clot.

Other potential candidates for an anti-fluke vaccine are hemoglobin, isolated from mature *Fasciola hepatica* (McGonigle and Dalton 1995) and cathepsin L secreted by adult *Fasciola hepatica* (Smith et al. 1993; Smith et al. 1994; Spithill 1995). Up to now, next to the irradiated *Fasciola gigantica* metacercariae (Bitakarami 1973) several antigens have been named as potential protein vaccines:

*Fasciola hepatica* hemoprotein

Fatty acid-binding protein Sm14 from *Schistosoma mansoni*

Thiol proteases with Cathepsin L-type activity

Glutathion S-transferase extracted from adult *Fasciola hepatica* polypeptide from *Fasciola* species (Gln-Xaa-Cys-Trp-Xaa)

Serin proteases with dipeptidyl peptidase activity

However, none of these potential candidates have emerged as an effective vaccine against *Fasciola hepatica* infection, and a large number of questions, such as: at what site in the host is immunity expressed?; against which stage of the parasite is immunity directed?; at which site in the host this immunity is induced?; which immune mechanisms are involved in protection?; which stage of *Fasciola hepatica* induces protective immunity?; and, last but not least, which antigens induce protection?, need to be answered before a successful vaccine can be developed. It is clear that answering these questions is greatly hampered by the lack of a suitable animal- or challenge model by which parasitic infections can be studied. And even when animal models are available progress can only be slow because of the fact that the parasitic infection in the host under study takes a considerable time to develop while its outcome depends on various factors that relate to the in time changing host-parasite relationship. For instance, although much focus has been directed to proteins, such as proteases, derived from newly excysted juvenile (NEJ) stages of *Fasciola hepatica* as candidate protective antigens (see, for instance, Tkalcevic et al. 1995), no clear cut identification of truly protective proteins has been foreseen. To the contrary, early developmental stages of *Fasciola hepatica* display rapid changes in protein and antigen expression during the early stages of infection, and such changes may even assist the parasite to evade the host immune response (Tkalcevic et al., Parasite Immunology 18:139-147, 1996). It has, for instance, been demonstrated that in parasites, proteases are involved in the invasion of host tissues, the evasion of immune attack mechanisms and help provide nutrients for parasite survival.

Thus, both the abundance of possible different proteins or antigens that need to be studied and the lack of suitable challenge models hamper the possible progress that is needed in the development of parasite vaccines. Crucial for progress in parasite vaccines are new methods to measure protective immunity in order to be able to study a variety of candidate protective antigens and to identify new candidate protective antigens. Thus, new animal models are needed that will increase the number of candidate proteins or substances that can be tested in time.

BRIEF SUMMARY OF THE INVENTION

The present invention provides a very rapid method to study, investigate and evaluate natural immunity against a parasite under study. The invention provides an ex vivo animal or challenge model method to rapidly study protective immunity directed against parasites and vaccines directed against parasitic infections. Ex vivo models are in general designed to study organs or organ systems of animals, under anesthesia, out of the context provided by the natural body, but still within the context of proper blood supply or the like. These models have in general a short execution time and provide less prolonged suffering to the experimental animal than seen with in vivo models.

The invention provides an ex vivo gut model in the rat, or in other small experimental animals such as mice or chickens, or in other animal species. Challenge parasites are injected in one or more ex vivo segments of the intestines of the selected animal and parasites, such as NEJs, that then penetrate the intestinal wall are recovered in a container that holds the particular gut segment. In particular, segments of the small intestine, such as duodenum, jejunum or ileum can be used, however, segments of other parts of the intestine, such as stomach, colon, cecum or rectum can also be used depending on the selected route of infection of the parasite under study. This model provided by the invention is capable of measuring expression of resistance in the entire intestine by comparing segments that have been subjected to different loads of parasites or to different stages of parasites. In addition, all the trajects in the migration route of the parasite such as can be found in gut mucosa, peritoneal cavity and liver and others, which are essential for the induction of mucosal resistance can be investigated. Such studies that are enabled by the invention provide knowledge about the most efficient vaccination route and about possibilities for an oral vaccine. Another advantage of the ex vivo challenge model using ligated gut segments is that migration of the pathogen from the gut lumen to the peritoneal cavity is limited to a small area, allowing the localization and characterization of the protective immune response against the parasite in the gut mucosa. Moreover, the level of resistance induced by a previous infection or vaccination can be correlated with immune mechanisms against the parasite (in the experimental part demonstrated with *Fasciola hepatica*) because the challenge infection does not settle and does not induce additional immune responses that interfere with those that need to be studied. Especially the immunity and protective mechanisms directed against those pathogens that penetrate mucosal or skin surfaces to infect the host, such as *Fasciola hepatica*, *Paragonimus westermani*, *Schistosoma mansoni*, *Toxocara canis*, *Dictyocaulus viviparus*, *Trichinella spiralis*, *Nematodiris* spp, *Nippostrongylus brasiliensis*, *Ascaris suum*, *Anisakis* and other pathogens varying from prions to protozoa, whether they may fully or partly penetrate the surfaces, can be measured specifically well by the model provided by the invention. Parasites or other pathogens that fully penetrate the mucosal surfaces of the gut segments employed in the model can be recovered as shown above, those that only partly penetrate the mucosal surfaces can be recovered from the blood or lymph vessels servicing the particular segment.

Measuring the immunity and protective mechanisms directed against parasites offers the possibility to modulate the effector phase of the immune response in the host which will result in the development of efficient vaccination strategies. In other words, the invention measures the capacity of proteins to be protective antigens for use as vaccine against infections. Because protection data are obtained the same day the ex vivo model provided by the invention enables quick testing of different stages of many candidate vaccine antigens (protective proteins or fragments derived thereof) for their capacity to induce resistance and immunity.

One such candidate vaccine antigen provided by the invention is a protective protein, or antigenic fragment derived thereof, the protein at least comprising an amino acid sequence derived of a proregion of an enzyme. Several proteases are involved when a parasite penetrates a mucosal or skin surface. Examples are serine protease, dipeptidyl peptidase-like protease, cysteine protease, proteases with cathepsin-like activity, but also enzymes like glutathion S-transferase and many others are involved during the phase when the parasite is penetrating a mucosal or skin surface. Surprisingly, the invention provides protective protein (fragments) derived of a proprotein of such an enzyme or protease which elicits a better immune response than when a mature enzyme is used. Optionally, it is possible to combine the immune response directed against the proprotein with the immune response directed against the mature enzyme.

BRIEF DESCRIPTION OF THE SEVERAL VIEWS OF THE DRAWINGS

FIG. 2: Nucleic acid sequences (2A) and deduced amino acid sequences (2B) of amplified cathepsin L proregions from different stages of *F. hepatica*, mRNA was isolated from adult flukes and newly excysted juveniles, respectively, and converted to cDNA. With primer set TGG CAT CAG TGG AAG CGA ATG // ATA ACC AGA TTC ACG CCA GTC (SEQ ID NOS: 7, 8), cathepsin L was amplified using adult *F. hepatica* cDNA as template (da13pro). With primer set TGG CAY GAR TGG AAR MGN ATG // RTA NCC RTA YTC NCK CCA RTC (SEQ ID NOS: 9, 10), the proregion of cathepsin L was amplified, using cDNA from newly excysted juveniles as template (da210 pro, da211pro). Amplified products were cloned into a pCR™ vector and sequenced. Nucleic acid sequences (Wijffels (SEQ ID NO: 19), da13pro (SEQ ID NO:21). da210pro (SEQ ID NO:23), and da211pro (SEQ ID NO:25) and deduced amino acid sequences of cathepsin L proregions obtained (Wijffels (SEQ ID NO: 20), da13pro (SEQ ID NO:22), da210pro (SEQ ID NO:24), and da211pro (SEQ ID NO:26) were aligned with the sequence from Wijffels et al. (1994).

FIG. 3: Alignment of cathepsin L proregions from *Fasciola hepatica* (SEQ ID NO: 27) (F-hep, Wijffels et al. 1994), *Schistosoma manosoni* (5-man1 (SEQ ID NO: 28), Michel, Klinkert and Kunz 1994; S-man2 (SEQ ID NO: 29), Smith et al. 1994), *Schistosoma japonicum* (SEQ ID NO: 30) (S-jap, Day and Brindley 1995) and *Homo sapiens* (SEQ ID NO: 31) (H-sap, Joseph et al. 1988). Amino acid residues that match *F. hepatica* sequence exactly are indicated by a box.

The proregion of *F hepatica* cathepsin L showed 41.8%, 38.5%, 30.8% and 20.2% homology with the cathepsin L proregion of *S. mansoni* (1), *S. Japonicum*, *H. sapiens* and *S. mansoni* (2), respectively.

Figure 4:
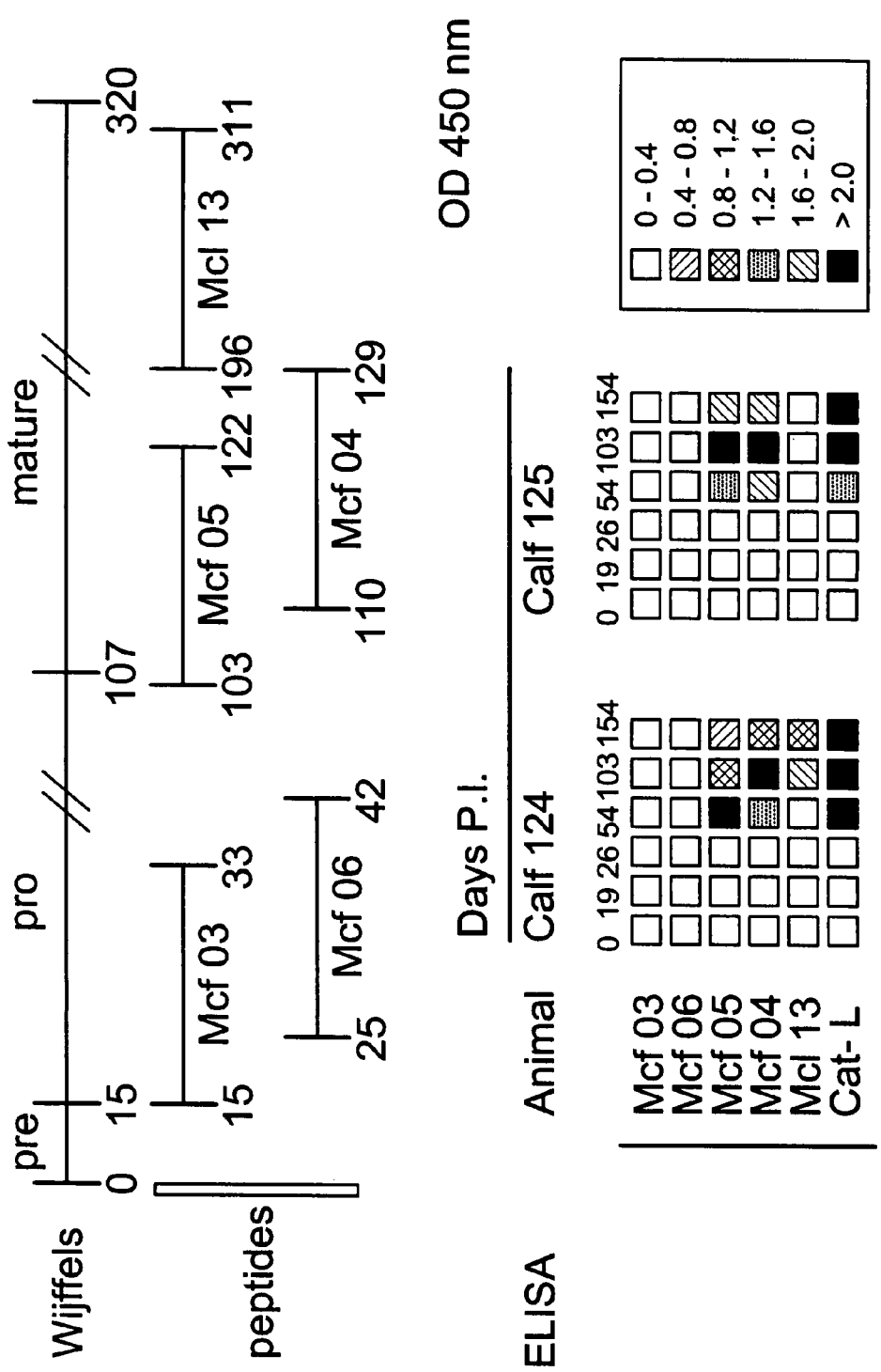

FIG. 4: Schematic representation of synthetic peptides derived from cathepsin L, and their reactivity with sera from *F. hepatica* infected calves, tested by ELISA. Five synthetic peptides of cathepsin L were produced, according to the amino acid sequence from Wijffels et al. (1994), representing possible immunogenic regions on the cathepsin L molecule (based on the antigenicity index from Jameson and Wolf). Peptides and purified cathepsin L, respectively, were coated onto ELISA plates and tested with sera (1/50 dilution) from two calves, sampled at regular intervals after infection with *F. hepatica*. Strong reactivity (OD value>0.8) of both calves was detected with both peptides MCF05 and MCF04 and with purified cathepsin L, from 54 days after infection.

FIG. 5: Sensitivity (A) and specificity (B) of *F. hepatica* peptide MCF04 ELISA.

A) Peptide MCF04, derived from cathepsin L (FIG. 4), was coated onto ELISA plates and tested with sera from five sheep, sampled at regular intervals after infection with *F. hepatica*. From week 5 after infection, OD-values increased and remained high until at least week 16 after infection.

B) Peptide MCF04 was coated onto ELISA plates and tested with sera from sheep, infected with *Fasciola hepatica* (n=5), *Echinococcus granulosus* (n=9), *Nematodirus battus*

(n=3) *Haemonchus contortus* (n=12), *Toxoplasma gondii* (n=12), *Eimeria* spp. (n=12), *Ostertagia circumcincta* (n=8), *Cooperia oncophora* (n=12), *Taenia ovis* (n=8), and with parasite-free sheep (n=12).

DETAILED DESCRIPTION OF THE INVENTION

In a preferred embodiment of the invention, the invention provides protective protein(fragments) derived of a proregion of such an enzyme, preferably a protease. In yet another embodiment, the immune response directed against the proregion is combined with the immune response directed against the mature enzyme.

One such candidate vaccine antigen provided by the invention is a protective protein, or antigenic fragments thereof, derived from NEJs of *Fasciola hepatica*. The protective status of rats vaccinated with candidate vaccine antigens, such as can be prepared from NEJ proteins, can be measured via vaccination studies using the ex vivo model provided by the invention, for example, by measuring the protective status of rats previously immunized with a selected protein. Various proteins derived from NEJs of *Fasciola hepatica* and isolated, for instance via SDS-PAGE gel electrophoresis and electroblotting, or via exclusion by molecular size, or filtration, and further identified by apparent molecular weight and by N-terminal sequencing can be studied. The invention, as an example, provides among others a protective protein or fragments thereof corresponding to an immunodominant protein found with NEJs with an apparent molecular weight of 30 to 32 kD and an N-terminal amino acid sequence of XXDVSW-PFWDRMYNY (SEQ. ID NO:1) (amino acids are listed in the one-letter code, x=unknown amino acid). Also provided by the invention are nucleotide sequences encoding protective proteins or (poly) peptides provided by the invention.

A preferred embodiment of the invention is a protective protein, or fragments thereof, which protein is at least comprising an amino acid sequence derived of a proregion or prosequence of a protease, for example, a protease which is (at least partly) encoded by a nucleic acid having a nucleotide sequence corresponding to a nucleotide sequence as shown in FIG. 2.

Methods to derive such sequences from (partly) isolated or identified (parasite)proteins are known in the art, for example, it is possible to identify immunogenic determinants or fragments by studying the antigenicity index by, for example, computer analysis. Furthermore, nucleotide sequences encoding the enzymes or proteases are known in the art. Sequences encoding cathepsin-like proteases are, for example, shown by Wijffels et al. (1994). Often, a part of a sequence encoding a mature enzyme is known, which enables an average skilled artisan to identify corresponding nucleic acid sequences encoding corresponding pre- and/or proregions. Such nucleic acid and/or protein sequences can be obtained from both adult or juvenile stages of an organism. A preferred embodiment of the invention provides a protective protein, or fragments thereof, corresponding to a proregion derived of a protease mainly found in a juvenile stage of a parasite, preferably the parasite being a *Fasciola* species. By using isolated nucleotide sequences in amplification or screening methods, varying or different parasitic sequences that encode functionally equivalent proteins or (poly) peptides can be identified in and isolated from related parasites. All such nucleotide sequences or fragments thereof can be molecularly cloned by methods known in the art in suitable expression systems to generate recombinant proteins that can be used in anti-parasite vaccines or for diagnostic purposes, as described above.

An example of an immunogenic determinant or fragment or fragments as provided by the invention is a fragment derived of a proregion of a protease. A typical example is a peptide corresponding or related with a peptide, such as MCF03 or MCF06, or a peptide found at an overlapping position, in a proregion of a protease, examples can also be found in FIGS. 2 and 3. Other corresponding fragments or peptides can be found in related (proregions of) proteases. In the experimental part such peptides that are derived of a proregion of a cathepsin-like protease are described. It is well known in the art that synthetic peptides can be rendered more immunogenic by replacing amino acids with others. Also deletion or insertion of (an) amino acid(s) in such peptides is practiced. Guidance can be found by using techniques such as PEPSCAN, or replacement-net mapping, in this way more immunogenic peptides are derived from original peptide sequences. Immunogenicity can further be increased by replacing L-amino acids by D-amino acids. In a preferred embodiment of the invention, such vaccines comprise at least a protein or (peptide) fragment thereof derived from a proregion of cathepsin-like proteases (such as Cathepsin B, H, L, S), for example, derived from *S. Mansoni, Tryponasoma Cruzei* or *T. Congolense*, or vertebrate cathepsin derived, for example, from chicken, rat or human lives, or other cathepsin-like proteases. Cleavage sites, identifying the pre- and proregions of such proteases can easily be found by comparing sequence characteristics and, for example, by following Von Heijne's rule. Assessment or measuring of the protective value or capacity of such proteins or vaccines can of course be performed in the ex-vivo model also provided by the invention. The nucleotide sequences alone, or incorporated in suitable vector systems or constructs can also be employed in DNA vaccination protocols. Such sequences can for instance be derived by amplification techniques, such as PCR, using degenerate primers deduced from (partly) known amino acid sequences corresponding to protective proteins provided by the invention. Amplified nucleotide fragments can be cloned and sequenced via standard techniques and so provide the isolated nucleotide sequence of genes or fragments thereof encoding the protective proteins or (poly) peptides provided by the invention. Such proteins or fragments can, in isolated and/or recombinant form, be used as vaccine antigens, alone or in combination with other preparations serving as vaccine or can be used as diagnostic antigen in diagnostic tests. Also, antibodies, be they polyclonal or monoclonal or synthetic antibodies or antibody fragments specifically directed against or prepared against protective proteins or (poly) peptides provided by the invention are part of the invention.

Furthermore, a diagnostic test comprising the protective protein or an antibody directed against the protein or a nucleotide encoding the protein are also part of the invention. Furthermore, a diagnostic test which measures proteins excluding the protein, or antibodies against proteins, excluding antibody directed against the protein, and wherein the diagnostic test is specifically designed to be used as an accompanying test to the use of a vaccine which specifically includes the protein is also part of the invention. With such an accompanying test infected animals can be differentiated from vaccinated animals. An example of such a diagnostic test is given in the experimental part in this description. Herein it is shown that antibodies directed against an protective epitope derived from a proregion can be differentiated from antibodies directed against the mature part of the enzyme, allowing the differentiation of infected animals from vaccinated animals. It is of course preferred that the animals are vaccinated with a vaccine comprising a protein (fragment) derived of a proregion of an enzyme, such as a protease, as provided by the invention. Such differentiation is not possible when animals are vaccinated with a (mature) protease with enzymatic activity.

In a preferred embodiment of the invention, a vaccine comprises mainly a protein (fragment) derived of a proregion of a protease, where as a diagnostic test comprises mainly a protein (fragment) derived of a mature enzyme part of the protease, whereby combining such a vaccine with such a test allows controlled eradication of a parasite infection.

In addition, the invention provides a diagnostic test measuring an antibody directed against an immunodominant, species specific, epitope on a cathepsin-like protease, preferably wherein, the species is *Fasciola hepatica*. The test, comprising, for example, a peptide corresponding to peptide MCF04, or a peptide related thereto, allows, for example, biological differentiation of animals infected with *Fasciola hepatica* from animals injected with other parasites, such as *D. viviparus*, which otherwise have a strong immunoreactivity with Cathepsin-L protease as a whole.

As described herein above, and further described in the experimental part of this description, without limiting the invention thereto, the invention among others provides a protective protein, or antigenic fragment derived thereof, and related nucleic acid sequences, that are at least comprising and/or encoding an amino acid sequence derived of or proregion of an enzyme, such as a protease, for example, for inclusion in a vaccine, for example, in parasitic infections. The invention also provides use of such a vaccine in animals, preferably mammals. Vaccine candidates are, for example, vaccines for protection against parasitic infection in ruminants, such as those susceptible to *Fasciola* infections, or in humans, such as those susceptible to *Schistosoma* infections.

EXAMPLES

Experimental Part

Materials and Methods

Rats

Specific pathogen free female Wistar rats (Charles River, Sulzfeld) were selected for all experiments. Rats were provided with food and water ad libitum. Rats were food deprived during 16 hours before primary and challenge infection. Rats were six weeks of age at the time of primary infection or first vaccination. Rats were ten weeks of age at the time of the challenge infection, with the exception of rats used to study the duration of resistance. These rats were 19 weeks old at the time of challenge infection.

*Fasciola hepatica*

*Fasciola hepatica* metacercariae were produced within the ID-DLO institute. In vitro excystment of metacercariae was performed by the method of Smith and Clegg (1981). NEJs were counted under a microscope (magnification 160×) directly after excystment. NEJs were kept in 300 µl of RPMI-1640 culture medium (ICN-Biomedicals BV, Zoetermeer, Holland) at 37° C. until use (less than one hour after excystment).

Primary Infection

Twenty-five *Fasciola hepatica* metacercariae were orally administered to rats in 1 ml of tap water. After delivery of the pathogen syringe and cannula were flushed to check delivery of the metacercariae. Metacercariae that stayed behind were administered in another ml of tap water.

Expression of Resistance

Total resistance: quantification of the number of challenge parasites reaching the target organ, the liver.

To measure the total level of protection against *Fasciola hepatica* rats were orally challenged with exactly 200 metacercariae. After delivery of the pathogen syringe and cannula were flushed to check delivery of the metacercariae. Metacercariae that stayed behind were administered in another ml of tap water. Three weeks after challenge, infection rats were killed, livers removed and placed in separate petri-dishes containing 50 ml of RPMI-1640 culture medium. Livers were incubated at 37° C. Every hour (up to six hours), livers were cut into smaller pieces and placed in new petri-dishes. NEJs recovered were counted.

Resistance at Gut Level: Quantification of the Number of NEJs Penetrating the Gut Wall, Using an Ex Vivo Infection Model Rats were anaesthetized by ether inhalation and immediately thereafter injected with 50 mg/kg of nembutal (Compagnie Rousselot, Paris, France) intraperitoneally and 0.05 mg/kg of atropin (AUV, Cuyk, Holland) subcutaneously. During the experimental procedure, additional nembutal (16 mg/kg) was injected subcutaneously three hours after ether inhalation. Forty-five minutes after anesthetization, an incision (1.5 cm) was made below the diaphragm and a loop of the small intestine of about 7 cm in length was taken out of the body cavity. A segment or segments of about 5 cm was delimited with two linen threads (B. Braun, Melsungen AG), at standard locations from the stomach. To study resistance at different locations in the intestine, segments of the duodenum (1 to 5 cm from the stomach; n=6), the mid jejunum (40 to 60 cm from the stomach; n=6) and the ileum (70 to 90 cm from the stomach; n=6) were prepared. In the segment or segments NEJs were injected according to the method of Burden et al. (1983). After injection, needle and syringe were flushed three times with 1 ml of medium in a petri dish. NEJs that remained behind in syringe and/or needle during inoculation were quantified under a microscope (rest fraction), and the infection dose was calculated (counted dose minus rest fraction).

During the experiment, the gut loop or loops including the segment or segments was or were kept outside the body cavity and the incision was closed with one or two surgical staples. Per experiment, eight rats were laid onto perspex plates, the gut loops were led through holes in the plates and hung freely in 50 ml beakers well below the surface of RPMI-1640 medium. The beakers with 50 ml medium were changed every hour and NEJs that had migrated through the gut wall into the beaker were quantified by light microscopy (peritoneal fraction; magnification 100×). During the experiment, the whole system was kept at body temperature: 1) by placing the beakers in a water bath of 37° C., 2) by warming the rats pumping warm water from a central heater below the perspex plates on which the rats were laying and 3) by warming the rats using an infrared lamp, when necessary as indicated by measurement of the body temperature. The rats were killed after six hours, gut segments removed and segment size and distance to the stomach determined. The lumina of the segments were flushed with medium and NEJs remaining in the gut lumen were quantified by light microscopy (luminal fraction). The segments were finally fixed according to the "Swiss roll" method (Bexter, 1982) in methylbutane (−150° C.) and stored at −70° C. for immunohistochemistry.

Reproducibility of the Ex Vivo Gut Model

To determine the number of NEJs left in the gut wall (gut fraction) after the experiment, each gut segment was cut into 10 µm frozen sections. Every fifth section was collected to score any NEJ (size NEJ±100 μm), air-dried and fixed for ten minutes in acetone (Merck). Fixation and all subsequent washings and incubations were performed at room temperature. After fixation peroxidase activity in the gut wall was blocked: sections were incubated for 20 minutes in 0.1 M Tris-HCl pH 7.5, containing 2% $NaN_3$ and 0.2% $H_2O_2$. Sections were then washed for five minutes in three changes of Tris-buffered saline pH 7.4 (TBS), stained for five minutes in 0.1 M Tris-HCl pH 7.5, containing 1 mg/ml 3,3'-diaminobenzidine (Sigma, St. Louis, USA) and 0.015% $H_2O_2$, washed for five minutes in three changes of phosphate-buffered saline pH 7.6 (PBS) and incubated for one hour in PBS containing 2% normal rat serum (NRS) and 4% bovine immune serum. This serum was raised in a five-month-old calf by two oral infections with 4500 and 2250 *Fasciola hepatica* metacercariae, with an interval of 11 weeks. Antiserum was obtained eight weeks after the second infection. After three washings with PBS, sections were incubated for one hour with peroxidase-conjugated rabbit anti-cow immunoglobulin (Dakopatts, Glostrup, Denmark), diluted 1:500 in 2% NRS in PBS. Subsequent washing was performed and peroxidase activity was visualized by an eight-minute incubation in a freshly made, filtered solution of 0.05 M NaAc pH 4.4, containing 0.2 mg/ml 3-amino-9-ethylcarbazole (Sigma, St. Louis, Mo., USA) and 0.015% $H_2O_2$. After staining, the sections were washed in running tap water and mounted in aquamount (BDH Laboratory supplies, Poole, England). Microscopically counting of NEJs was performed and successive sections were compared to prevent scoring NEJs twice.

Induction of Resistance

Gut Level

1) Five rats were orally infected with 25 metacercariae and treated four hours later with the flukicide triclabendazole (100 mg/kg, Fasinex, CIBA-GEIGY, Basel, Switzerland). Flukicide treatment was repeated the following three days. After five weeks expression of resistance at gut level was measured, using the ex vivo gut model, and "breakthrough" infections in the liver were investigated at autopsy. To confirm that Fasinex treatment did not influence migration of the challenge parasites through the gut wall, non-infected, fasinex-treated rats were used as challenge controls.

2) Four rats were primed with 18 to 25 NEJs directly in the jejunum. During four hours, NEJs penetrating the gut wall were captured using the ex vivo gut model. During primary infection, rats were anesthetized by an intraperitoneal injection with ketamine (40 to 60 mg/kg; Alfasan, Woerden, NL), and a subcutaneous injection with xylazine (3 to 8 mg/kg; Rompun, Bayer, Germany) and atropine (0.05 mg/kg). One day before and one day after infection, rats were treated with the antibiotic duoprim (0.5 ml/kg, subcutaneously; Pitman-Moor, Houten, NL). The sedative fiadyne (1 mg/kg, intramuscularly; Schering-Plough, Amstelveen, NL) was given the first three days after infection. After four weeks expression of resistance at gut level was measured and "breakthrough" infections in the livers were investigated at autopsy.

Peritoneal Cavity/Liver

NEJs of the primary infection were injected in the peritoneal cavity (n=3, 13 to 17 NEJs) or between the liver lobes (n=8, 7 to 25 NEJs). For liver infection, a small incision (1 cm) was made below the diaphragm. NEJs in 100 μl of RPMI-1640 were injected between the liver lobes. During the operative procedure rats were anaesthetized as described above. For intraperitoneal infection rats were anesthetized by ether inhalation and immediately thereafter intraperitoneally injected with the NEJs.

Preparation of *Fasciola Hepatica* Antigen Extracts

After in vitro excystment, NEJs were washed with PBS. Three hundred mg of NEJs in 3 ml of PBS were sonicated (Sonicor UPP-400, Sonicor Instrument Corporation-copaque, NV) five times for 30 seconds at 20 kHz on ice. The suspension was extracted over night at 4° C. and thereafter sonicated again. The extract was centrifugated for 20 minutes at 10,000 g and the supernatant stored in aliquots of 1 ml at −70° C. Concentration of protein in the extract was 3 mg/ml, as determined by a Bradford assay.

Adult *Fasciola hepatica* were obtained from the livers of cattle and thoroughly washed with HMEM-medium and subsequently with PBS at 4° C. Flukes were ground using a Sorvall omnimixer (model 17106) ten times for 30 seconds on ice. The subsequent sonification and extraction procedures were performed as described above.

YM-30 Filtration NEJ-Antigen

Freshly prepared NEJ extract (10 ml of a 3 mg/ml extract) was diluted in PBS to a volume of 30 ml and filtrated through a YM-30 membrane (Amicon, 62 mm) at 1 Bar, at 16° C. (Amicon model 8200). The 5 ml rest fraction was replenished with 5 ml of PBS and filtrated again to a 5 ml rest fraction. This procedure was repeated two times. Finally, the 40 ml filtrate (25 μg/ml) was stored at −70° C. in aliquots of 1 ml. Other filtrates, containing more protein, i.e., 183 μg/ml were prepared and stored likewise.

Vaccination Regimes

Rats were primed with 100 μg of NEJ or adult stage *Fasciola hepatica* antigen intraperitoneally. After three weeks, an intraperitoneal boost immunization with 500 μg of antigen was given. One week after the boost, immunization resistance against a challenge infection was determined. To measure the total level of protection rats were orally challenged with 200 metacercariae and to measure the level of protection expressed at gut level rats were intrajejunally challenged with NEJs (for recovery procedures see "expression of resistance").

Doses of the YM-30 filtrate used were 20 μg and 65 μg for primary and boost immunization, respectively.

SDS-PAGE and Western Blotting

Sodium dodecyl sulfate polyacrylamide gel electroforesis (SDS-PAGE) was performed using the Tris-Tricine buffer system (Schagger and von Jagow, 1987) with 10% to 20% (w/v) polyacrylamide gradient gels or 15% slab gels (8 by 10 cm). 12.5 μg of protein was applied per gel in the presence of β-mercaptoethanol. To determine the molecular weights of the NEJ proteins a prestained MW marker from BRL (Bethesda Research Laboratories, Breda, The Netherlands) was added to the gel (MW range: 14.3-200 kD). After electrophoresis at 20 mA for 3.5 hours, separated proteins were electrophoretically transferred (16 hours, 20 mA, RT) onto a polyvinylidene difluoride (PVDF)-type membrane (Applied Biosystems, Inc) using a buffer system, containing 10 mM 3-cyclohexylamino-1-propane-sulfonic acid (CAPS) pH 11 (Aldrich) in 10% methanol.

N-Terminal Sequencing

Blotted proteins were visualized by staining with 0.1% Coomassie Brilliant Blue R-250 (Sigma). The regions staining with CBB or the protein band staining in immunoblotting with the sera were excised from the PVDF-membrane and 2 cm membrane was subjected to Edman degradation sequencing using an Applied Biosystems Protein Sequencing system (model 476A). Analysis was performed at "The Centre for Biomembrane and Lipid Enzymology, Department of Biochemistry, University of Utrecht."

Immunostaining

Four immunostaining 4 mm PVDF-strips were saturated for one hour with 10% normal rabbit serum (NRS) in PBS-0.5 M NaCl-0.05% TWEEN®-80, pH 7.2 (PBS-NT). Subsequently strips were incubated for 16 hours with 40 µl rat serum or 40 µl calve serum in 2 ml of PBS-NT containing 2% NRS. The calf sera were obtained from five-month-old calves, 12 weeks after oral infection with 4500 Fasciola hepatica metacercariae. After a three-hour incubation with 20 µg of mAb anti-rat IgG1 (culture supernatant, TNO Leiden, The Netherlands) and 16 µg of mAb anti-bovine IgG1 (van Zaane et al.) in 2 ml PBS-NT containing 2% NRS, HRPO-conjugated rabbit anti-mouse Ig (Dakopatts), 1/500 diluted in PBS-NT containing 2% normal rat serum was added for two hours. Chloronaphtol (Sigma; 0.5 mg/ml 4-Chloro-1-naphtol and 0.015% $H_2O_2$ in Tris-buffered saline pH 7.4) was used as substrate. One hour after application of the substrate staining was stopped by washing the strips with aqua dest.

All incubations were performed at room temperature and between all incubation steps strips were washed three times during ten minutes with PBS-NT.

Peptide Synthesis

Reagents

N-methylpyrrolidone (NMP), N,N-dimethylformamide (DMF), N-hydroxybenzotria-zole (HOBt), 2-(1H-benzotria-zol-1-yl)-1,1,3,3-tetramethyluronium hexafluorophosphate (HBTU) and piperidine were peptide synthesis grade and obtained from Perkin Elmer/ABI (Warrington, UK). Acetonitrile was gradient grade, diisopropylethylamine (DIEA), trifluoroacetic acid (TFA), thioanisole (TA), phenol, and ethanedithiol (EDT) were synthesis grade and were obtained from Merck (Darnstadt, Germany). Before use, diethyl ether was purified over a column of activated basic aluminum oxide and DIEA was distilled twice over ninhydrin and potassium hydroxide. Fmoc-amino acid derivatives and Rink resin (4-(2',4'-dimethoxyphenyl-Fmoc-amino methyl)phenoxy resin) were obtained from Saxon Biochemicals (Hannover, Germany).

Peptide Synthesis

Five synthetic peptides were produced of about 20 amino acids in length, according to the sequence of cathepsin L from Wijffels et al. (1994). The peptides were derived from possible immunogenic determinants on the molecule, based on the antigenicity index as described by Jameson and Wolf. Peptides MCF03 and MCF06 were derived from the prosequence of cathepsin L, peptides MCF05, MCF04 and MCL13 from the enzymatic part of the molecule. Peptide MCF03 included aa 15 to 33 (Gly-Ser-Asn-Asp-Asp-Leu-Trp-His-Gln-Trp-Lys-Arg-Met-Tyr-Asn-Lys-Glu-Tyr-Asn) (SEQ ID NO:2), peptide MCF06 aa 25 to 42 (Lys-Arg-Met-Tyr-Asn-Lys-Glu-Tyr-Asn-Gly-Ala-Asp-Asp-Gln-His-Arg-Arg-Asn) (SEQ ID NO:3), peptide MCF05 aa 103 to 122 (Ala-Asn-Asn-Arg-Ala-Val-Pro-Asp-Lys-Ile-Asp-Trp-Arg-Glu-Ser-Gly-Tyr-Val-Thr-Glu) (SEQ ID NO:4), peptide MCF04 aa 110 to 129 (Asp-Lys-Ile-Asp-Trp-Arg-Glu-Ser-Gly-Tyr-Val-Thr-Glu-Val-Lys-Asp-Gln-Gly-Asn-Cys) (SEQ ID NO:5) and peptide MCL13 aa 296 to 311 (Gly-Glu-Arg-Gly-Tyr-Ile-Arg-Met-Ala-Arg-Asn-Arg-Gly-Asn-Met-Cys) (SEQ ID NO:6). The molecular masses of the peptides were in accordance with the expected values.

We used a Hamilton Microlab 2200 (Reno, Nev., USA) to synthesize up to 40 peptides simultaneously at 30 mmol scale. The Hamilton Microlab 2200 was programmed to deliver washing solvents and reagents to two racks with 20 individual 4 ml columns with filter, containing resin for peptide synthesis. The columns were drained automatically after each step by vacuum. The coupling cycle was based on Fmoc/HBTU chemistry (Fields et al. 1991) using double coupling steps of 40 minutes. Peptides MCF03, MCF06 and MCF05 were synthesized with an additional cysteine at the N-terminus. After coupling of the last amino acid, the Fmoc group was removed using 30% (v/v) piperidine/NMP for three and for 15 minutes. The peptides were washed with NMP (five times), acetylated using NMP/acetic anhydride/DIEA (10/1/0.1; v/v/v) for 30 minutes, washed successively with NMP and ethanol, and then dried. Peptides were deprotected and cleaved in two hours using 1.5 ml of a mixture of TFA/phenol/TA/water/EDT (10/0.75/0.5/0.5/0.25; v/w/v/v/v/) and then precipitated twice by adding hexane/diethylether (1/1; v/v). The precipitate was dried and lyophilized from water/acetonitrile (1/1; v/v).

HPLC and Mass-Spectrometry

For analytical HPLC we used two Waters pumps model 510, a Waters gradient controller model 680, a Waters WISP 712 autoinjector, and a Waters 991 photodiode array detector. A micromass Quattro II sq mass spectrometer, coupled with the HPLC system, was used to determine the molecular masses of the individual peaks by electrospray ionization. The products were analyzed in a linear gradient from 10% (v/v) acetonitrile/water with 0.1% (v/v) TFA to 70% (v/v) acetonitrile/water with 0.1% (v/v) TFA in 30 min on a Waters Delta Pak C18-100A (3.9×150 mm, 5 mm) column at 1 ml/minute.

Conjugation of Peptides to Keyhole Limpet Haemocyanin (KLH)

Peptides were conjugated to KLH carrier protein, using m-maleimidobenzoyl-N-hydroxysuccinimide ester (MBS). To 1 mg of KLH (Calbiochem, 10 mg/ml in 0.1 M phosphate buffered saline pH 7) 100 ml of MBS (Pierce, 40 mg/ml in dimethylformamide (Merck)) and 300 ml of acetonitrile were added in drops and the mixture was incubated for one hour on ice. Then 1.1 ml of PBS was added and the activated carrier was separated from excess MBS using a PD10 column (Pharmacia). One mg of peptide was added to 2.3 mg of activated KLH and incubated for one hour at room temperature. Then peptide and conjugate were separated by dialysis against PBS and the conjugate stored at −20° C.

Vaccination of Rats with Synthetic Peptides Derived from Cathepsin L

Rats (four per group) were vaccinated in the hind thigh muscles with 100 mg of peptide (i) in PBS, (ii) mixed with specol (ID-DLO, Lelystad), according to the manufacturer's instructions, (iii) coupled to KLH and mixed with specol. After three weeks, an intraperitoneal boost immunization was given with 100 mg of the corresponding peptide, without the use of specol. One week after the boost immunization rats were challenged orally and the parasite load in the liver was measured three weeks later.

PCR, Subcloning and Sequencing mRNA was isolated from 450 µl of packed NEJs (±45.000 NEJs) and two adult F. hepatica, respectively, using a Quick-Prep mRNA Purification Kit (Pharmacia Biotech).

cDNA was produced using a First-Strand cDNA Synthesis Kit (Pharmacia Biotech). The PCR amplification reactions were performed in 25 µl reaction volumes of PCR buffer II (perkin Elmer) containing 100 ng of cDNA, 2.5 mM $MgCl_2$, 200 µM-dTNPs, 1.08-1.46 µM of F. hepatica specific primers or 1 µM oligo (dT), and 0.5 unit of Taq DNA polymerase gold (Perkin Elmer). The sequences of the oligonucleotide primer sets, used to amplify the specific cathepsin L sequences were the following:

| | Cathepsin L sequence | primer set sequences (5'-3') | | |
|---|---|---|---|---|
| (i) | prosequence adult *F. hepatica* | TGG CAT CAG TGG AAG CGA ATG<br>ATA ACC AGA TTC ACG CCA GTC | (fw)<br>(rv) | (SEQ ID NO:7)<br>(SEQ ID NO:8) |
| (ii) | proprotein adult *F. hepatica* | TGG CAT CAG TGG AAG CGA ATG<br>Oligo (dT) | (fw)<br>(rv) | (SEQ ID NO:7) |
| (iii) | prosequence NEJ | TGG CAY GAR TGG AAR MGN ATG<br>RTA NCC RTA YTC NCK CCA RTC | (fw)<br>(rv) | (SEQ ID NO:9)<br>(SEQ ID NO:10) |
| (iv) | proprotein NEJ | TGG CAY GAR TGG AAR MGN ATG<br>Oligo (dT) | (fw)<br>(rv) | (SEQ ID NO:9) |
| (v) | proprotein NEJ | TGC CCN TTY TGG AAR MGN ATG<br>Oligo (dT) | (fw)<br>(rv) | (SEQ ID NO:11) |

The amplification reactions were performed in a preheated Perkins Elmer Cetus DNA Termal Cycler (80° C.), ten minutes at 92° C. followed by 30 cycles of 30 seconds at 94° C., 30 seconds at 62° C. and two minutes at 72° C.

Amplified fragments were inserted by TA cloning into the LacZ gene of a pCR™ II vector, according to the manufacturer's instructions (TA Cloning Kit, Invitrogen). After transformation of TA Cloning One Shot competent cells, clones harboring inserts were distinguished by their white color. To verify size of the inserts, plasmid DNA was isolated using the Wizard Plus SV Minipreps DNA Purification System (Promega) and digested by BamHI and EcoRV (Pharmacia LKB Biochemicals), according to the manufacturer's instructions.

Sequencing of the cloned material was done using the chain termination reaction described by Sanger et al. (1977). Of each product, at least two positive clones were sequenced, using both the M13 Reverse and Forward primers. Using these primers, we were not able to sequence the whole pro-cathepsin L molecule at one go. Additional primers (5'-3') were designed, based on the nucleotide sequences obtained, to sequence the missing parts:

```
NEJ:
                                                (SEQ ID NO:12)
ATC AGG GAC AAT GGT TCC
(fw; position 398-417)

(SEQ ID NO:13)
GAA GTG AGA TTG AGG ATC CAC
(rv; position 752-772)

(SEQ ID NO:14)
CAA TAC AGG AAA GAG CTT GG
(fw; position 638-657)

adult:
                                                (SEQ ID NO:15)
ACT GTG GTT CCT GTT GGG C
(fw; position 407-425)

(SEQ ID NO:16)
GTG TGA ATA AAT ACC ACT CCT G
(rv; position 779-800)
```

Of these primers, the use for either forward (fw) or reversed (rv) sequencing is indicated, as is their position with respect to the cathepsin L sequence from Wijffels et al. (1994).

Cathepsin L Peptide Enzyme Linked Immunosorbent Assay (ELISA) for the Diagnosis of *F. hepatica* Infection in Cattle and Sheep Experimental Sera To obtain mono-specific anti-*Fasciola* sera, 24 Holstein Frisian calves of five to eight months of age, reared free of parasites, were infected with 100 to 3000 *F. hepatica* metacercariae. Serum samples were taken at weekly intervals. Calves were monitored for infection by weekly counting of the number of eggs in the feces. At slaughter, flukes were detected in the bile duct of all calves. In addition, four- to eight-month-old calves were mono-infected with *D. viviparus* (Dv; n=4), *Ostertagia ostertagi* (n=1), *Nematodirus helvetianus* (n=1), *Cooperia oncophora* (n=1) or *Ascaris suum* (n=1). Serum samples were taken when all the infected cattle shed parasite eggs or *D. viviparus* larvae. Detailed information on these sera is provided elsewhere (de Leeuw et al. 1993).

Five ewes of the Texel Sheep Breed, between three and twelve months of age, reared free of parasites, were infected with 20 *F. hepatica* metacercariae. Serum samples were taken at weekly intervals. Sheep were monitored for infection by weekly counting of the number of eggs in the feces. At slaughter, flukes were detected in the bile duct of all sheep. Mono-specific sera against *Haemonchus contortus* (n=12) originated from sheep infected repeatedly (five to 50 times) with doses of 5,000 to 20,000 larvae. Antisera against *Ostertagia circumcincta* (n=8) originated from sheep infected once with 30,000 larvae. Monospecific sera against *Taenia ovis* (n=8) originated from sheep that had grazed on a pasture contaminated with *T. ovis* eggs. Cysticerci were found in all sheep at slaughter. Monospecific sera against *Cooperia oncophora* (n=12) originated from sheep infected once with 20,000 larvae. Monospecific sera against *Nematodirus battus* (n=3) originated from sheep infected five times with 5,000 larvae. Blood samples were taken ten to 15 weeks after infection, when all infected sheep shed parasite eggs or oocysts. Negative control sera were collected from parasite-free sheep (n=12).

Purification of Cathepsin L from Excretory/Secretory Products from *F. hepatica*

Adult flukes, collected from the bile ducts of experimentally infected cows, were washed three to four times, for one hour, with 0.01M PBS (pH 7.0). Twenty flukes were incubated per liter of HMEM medium containing streptomycin (100 µg/ml) and penicillin (100 IU/ml) at 37° C. for six days. The medium was refreshed each day and the supernatants collected from days 3 to 6 were pooled. This pool was centrifuged at 4° C. at 10,000 g for one hour and the supernatant stored at −70° C. until use. The average protein concentration was 10 µg/ml. The total protein yield was 1 mg per 10 g of flukes.

These excretion/secretion antigens were filtered through a YM-30 membrane (Amicon). The pH of the filtrate was adjusted to pH 9.5 with 0.5 M Tris-HCl pH 11, and subjected to ion exchange chromatography on a dyethylaminoethyl (DEAE)-Sephacel column (Pharmacia LKB, Uppsala, Sweden), equilibrated with 0.05 M sodiumcarbonate buffer, pH 9.5. After application of the filtrate, the DEAE-Sephacel column was washed with 0.05 M sodiumcarbonate buffer, pH 9.5, containing 200 mM NaCl. The column was subsequently eluted with the same buffer containing 500 mM NaCl. The eluate was subjected to SDS-PAGE, electroblotting and CBB staining and revealed one protein band. The 15 N-terminal amino acids, Ala-Val-Pro-Asp-Lys-Ile-Asp-Trp-Arg-Glu-Gln-Gly-Tyr-Val-Thr (SEQ ID NO:32), showed 95.4% homology to the cathepsin L sequence of Wijffels et al. (1994).

ELISA Procedure

ELISA plates (Greiner nr. 655001, Alphen aan de Rijn, The Netherlands) were coated with 100 µg of peptide MCF02, MCF03, MCF04, MCF05 and MCL13, respectively, in 0.01 M phosphate buffer (pH 7.5) and incubated overnight at 4° C. As a positive control, plates were coated with 100 µg of purified cathepsin L in 0.05 M carbonate buffer pH 9.5, and incubated overnight at 37° C. Between all incubation steps plates were washed three times with 0.05% TWEEN®-80 in tap water. An additional blocking step and drying off the plates was performed overnight by an "in-house method." One hundred µg of calve or sheep serum, diluted ⅟25 in 0.01 M phosphate buffer (pH 7.5), containing 0.05% TWEEN®-80 and 0.5 M NaCl, were added for one hour at 37° C. HRPO-conjugated monoclonal antibody against bovine IgG1 (⅟30; ID-DLO, Lelystad, NL) and polyclonal anti-sheep IgG (⅟15,000; Dakopatts) in 0.01 M phosphate buffer (pH 7.5) containing 0.05% TWEEN®-80, 0.5M NaCl and 1% normal horse serum, were added for one hour at 37° C. Tetramethylbenzidine (0.005% $H_2O_2$ and 1 mg/ml TMB in 0.1M Na-acetate/0.1 M citric acid buffer, pH 6.0) was used as substrate. Five minutes after application of the substrate, the reaction was stopped with 0.5 M $H_2SO_4$, and extinctions were measured at 450 nm in an Easyreader spectrophotometer (SLT, Vienne). The cut-off value between negative and positive was calculated as the average plus three times the standard deviation of the OD 450 nm of sera from parasite-free sheep or cows, respectively.

Results

Reproducibility of the Ex Vivo Gut Model

The accuracy of NEJ quantification in our infection and immunity model was tested in 18 rats. First, we determined the exact infection dose. After inoculation of an exact number of NEJs into a gut segment, NEJs remaining in needle and syringe were counted. This rest fraction, comprising on average 24% (range 6% to 56%) of the inoculation dose, was subtracted from the inoculation dose. Six hours after infection we determined the peritoneal fraction, the luminal fraction and the gut fraction (using an immunohistochemical procedure) and the sum of these fractions was compared with the infection dose (ranging from 4 to 78 NEJs/cm). The peritoneal fraction ranged from 4 to 33 NEJs/cm (43% to 80% of the infection dose, AVG 57%), the luminal fraction from 0 to 10 NEJs/cm (0% to 6%, AVG 1%), and the gut fraction from 0.2 to 19 NEJs/cm (6% to 44%, AVG 32%). The mean total sum of NEJs recovered was 87% (±3.6% SEM) of the infection dose, demonstrating the grade of reproducibility of the gut model.

Expression of Resistance

Infection with *Fasciola hepatica* results in resistance against a challenge at gut level.

Four weeks after oral infection with *Fasciola hepatica* rats were almost completely protected against a challenge infection. The number of challenge parasites that reached the liver of infected rats was reduced with 97% (±1.1% SEM; n=13), as compared to naive rats.

A large part of resistance against *Fasciola hepatica* was expressed in the gut mucosa, the porte d'entree of the parasite. Migration of NEJs through the intestinal wall of immune and naive rats was compared, using the ex vivo gut model. In immune rats resistance was expressed within two hours after challenge. After six hours, when migration was completed, 52% (±2.37% SEM; n=40) of the challenge NEJs had penetrated the jejunum of naive rats, whereas in immune rats only 12% (±1.77% SEM; n=40) had traversed the gut wall. Thus, as a result of infection NEJ migration through the jejunum wall was reduced with 78%. Considerable resistance was also detected in the duodenum (50% reduction in NEJ migration), mid jejunum (65% reduction) and ileum (75% reduction). Thus, the entire small intestine is an important immune barrier. The duration of resistance was at least three months (n=6).

Induction of Resistance

To investigate the site in the host where resistance against *Fasciola hepatica* is induced, we followed the infection route of the parasite: gut mucosa-peritoneal cavity-liver.

The role of gut penetration in the induction of resistance was investigated in the following way. After gut penetration of NEJs of the primary infection, further migration of NEJs to the liver was prevented by 1) flukicide treatment of the rats or 2) capturing the NEJs using the ex vivo gut model. Both flukicide treatment of the rats and capturing of NEJs after gut penetration prevented further migration to the liver, because four weeks after infection, all rats had healthy looking livers. Surprisingly, none of the rats were protected against a challenge infection. Thus, gut passage by itself does not induce resistance against *Fasciola hepatica* expressed in the gut mucosa.

After penetration of the intestinal wall *Fasciola hepatica* enters the peritoneal cavity and migrates towards the liver. This route was imitated by injecting NEJs of the primary infection in the peritoneal cavity or between the liver lobes. As a result, four weeks after infection all rats were highly resistant against a challenge infection. The average level of protection at gut level was 78.8% (±4.6% SEM; n=11). Apparently, immunity is induced in the route peritoneal cavity-liver and not during gut passage. Based on these results in later vaccination studies the antigen was injected in the peritoneal cavity.

Immune Mechanisms Against *Fasciola hepatica* in the Gut Mucosa

Gut segments of immune and naive rats were prepared for (immuno)histochemistry and compared for immunoglobulin, T cell, NK cell, goblet cell, macrophage, mucosal mast cell and granulocyte responses. In immune rats frequencies of mucosal mast cells, eosinophils and IgE-positive cells were significantly increased, as compared to naive rats. Upon reinfection of immune rats with *Fasciola hepatica* in a segment of the jejunum, challenge parasites are eliminated in the gut mucosa within two hours. At this time interval after infection challenge NEJs were coated with IgG1 and IgG2a antibodies. At the same time infiltrates of eosinophils were associated with the NEJs. Moreover, the level of protection at gut level strongly correlated with eosinophil responses in the gut mucosa and IgG1 responses directed against NEJ-antigen in the serum. These observations indicate that IgG1 (and IgG2a) antibodies and eosinophils are essential for protection.

Vaccination Studies

Stages of *Fasciola hepatica*

The developmental stage of *Fasciola hepatica* inducing the best protection was investigated. Extracts of NEJs and adult flukes were prepared and injected intraperitoneally. Antigens from the NEJ stage appeared far superior: 57.3% (±6.2% SEM; n=10) protection at gut level was achieved, whereas adult stage antigens resulted in only 13.3% (±6.2% SEM; n=11) protection.

To measure the total level of protection induced by antigens from both stages, challenge parasites reaching the target organ, the liver, were recovered. Using NEJ antigen as vaccine almost complete protection was achieved. The level of protection in these rats was 92.6% (±2.5% SEM; n=13). Adult stage antigens resulted in 56.3% (±15.9% SEM; n=8) protection.

Isolation of NEJ Antigen Fraction

Because immunoblot studies with sera from cattle and rats revealed two low molecular weight (LMW) NEJ antigens only recognized by immune rats (>70% protection), a limited NEJ antigen fraction was isolated by means of YM-30 filtration. During the procedure only 3% of the protein traversed the YM-30 membrane and the number of antigens was reduced from more than 50 to about five. Vaccination of rats with this LMW fraction resulted in 80% (±14% SEM; n=11) protection, based on the number of parasites that reached the target organ, the liver. Of the eleven rats tested, six rats were 100% protected, and all this without the use of any adjuvant! Also, at gut level, considerable resistance was expressed, 54% (±12% SEM; n=7).

Identification of Vaccine Antigens

To identify the protective antigens present in the YM-30 filtrate, proteins were separated by SDS-PAGE. After electroblotting of the proteins onto a PVDF membrane different parts of the membrane were used for immunoblotting, protein staining and N-terminal sequence analysis, respectively. Protein staining revealed five protein bands with approximate molecular weight of 30-32 kD, 28 kD, 25 kD, 20 kD and 12 kD, respectively. Of these proteins, only the 30-32 kD protein was recognized by all rats vaccinated with the YM-30 isolate (n=6), and was clearly immunodominant. Together with the observation that in natural immune rats challenge NEJs are coated with IgG1 antibodies and that the level of IgG1 in the serum is strongly correlated with protection, we conclude that this 30-32 kD protein is a protective antigen. The 30-32 kD protein was also recognized by orally infected rats (n=6), rats vaccinated with NEJ extract (n=6) and orally infected calves (n=6). On the contrary, the antigen was not recognized by rats vaccinated with adult stage antigens (n=3).

Vise versa, on immunoblots of the YM-30 filtrate obtained from adult flukes, no reaction was observed with sera from the vaccinated rats, infected rats or infected cattle.

The 30-32 kD protein band was excised from the PVDF-membrane and further identified using N-terminal sequencing. The protein displayed a N-terminal amino acid sequence comprising the sequence XXDVSWPFWDRMYNY (SEQ ID NO:1), in which the amino acids are given in the one letter code.

The N-terminal amino acids of the 30-32 kD immunogen showed 69% homology with the N-terminus of NEJ protein 4, as described by Tkalcevic et al. (1995), a 40 kD protein under non-reducing conditions. The N-terminus of the here disclosed 30-32 kD protein shows 54% homology with the prosequence of cathepsin L derived from adult *F. hepatica* (Wijffels et al. 1994). Characterization of the N-terminal of the 28 kD and 25 kD proteins from the PVDF membrane revealed the following sequences:
(i) XXWAVLVAGGSD (SEQ ID NO:17). This sequence shows 70% homology to the N-terminus of NEJ haemoglobinase, according to Tkalcevic et al. (1995)
(ii) DVPASIDWRQYGYVTEVKDQ (SEQ ID NO: 18). This sequence is 95% homologous to the N-terminus of NEJ cathepsin L according to Tkalcevic et al. (1995) and 80% homologous to the N-terminus (aa 107 to 126) of mature cathepsin L according to Wijffels et al. (1994).

The immunoblotting studies together with the N-terminal sequence analyses demonstrate that procathepsin L is an immunodominant, protective antigen, whereas the enzymatic active cathepsin L is only occasionally recognized by immune cattle or rats. We show here that the presence of the prosequence (proregion) of cathepsin L is crucial for immunogenicity and protection. Moreover, the studies indicate that procathepsin L derived from juvenile stages such as NEJs is more protective than procathepsin L derived from adult stages.

Vaccination of Rats with Synthetic Peptides Derived from Cathepsin L

Figure 1:
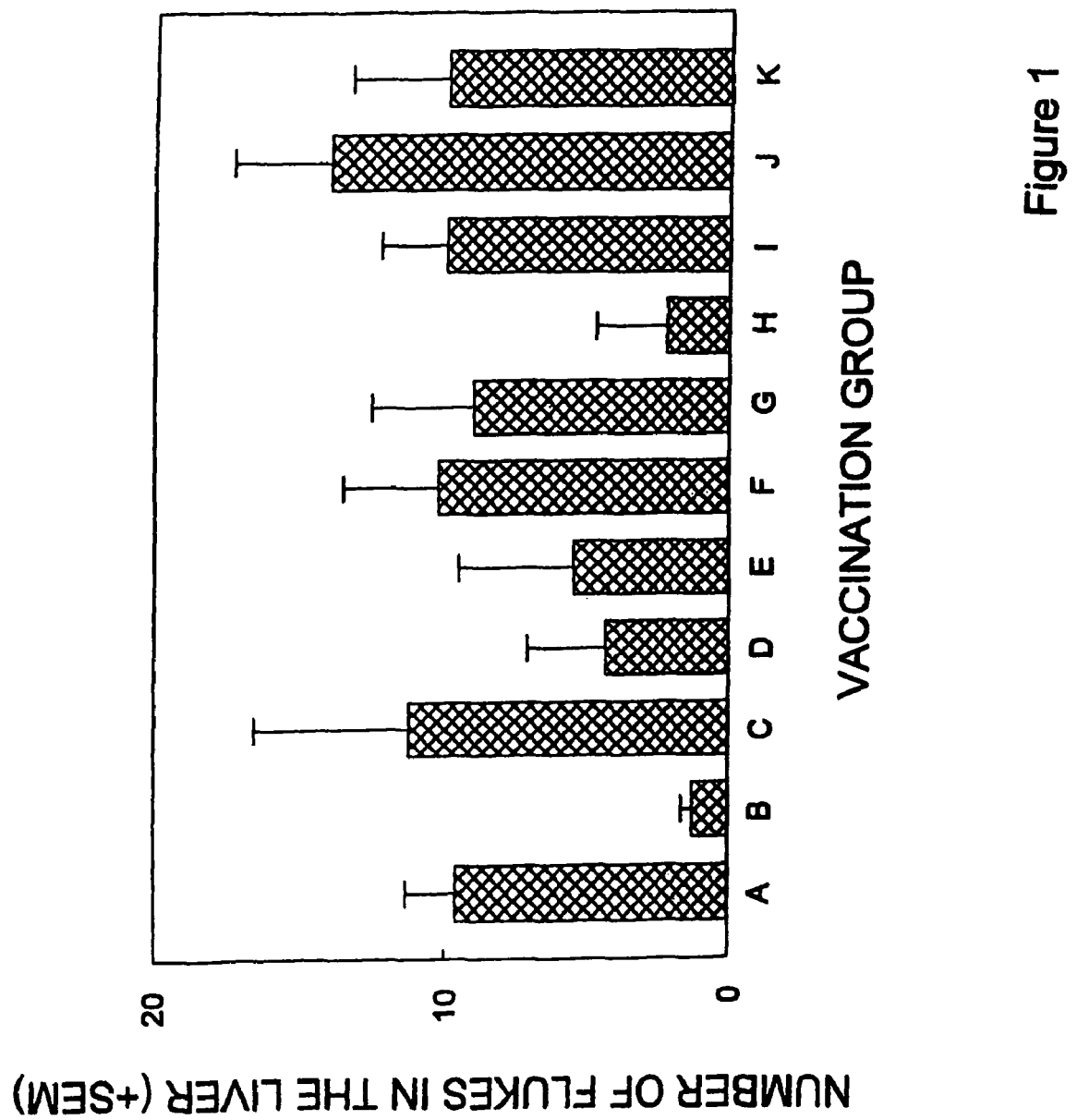
FIG. 1: Mean recovery (±SD) of *F. hepatica* in the liver three weeks after oral challenge of (a) non-immunized rats, (b) orally infected rats; rats vaccinated with (c) MCF03 (d) MCF03+specol, (e) MCF03-KLH+specol, (f) MCF06 (g) MCF06+specoll (h) MCF06-KLH+specol (i) MCF04 (j) MCF04+specol (k) MCF04-KLH+specol.

Rats were vaccinated with two synthetic peptides derived from the prosequence of cathepsin L, MCF03 (aa 15 to 33) and MCF06 (aa 25 to 42), and with a peptide derived from the mature enzyme, MCF04 (aa 110 to 129). When rats were vaccinated with peptide MCF03 or MCF06, these rats were protected against a challenge infection (FIG. 1). The best protection was obtained when the peptides were conjugated to a carrier and applied in the presence of adjuvant. However, when rats were vaccinated with peptide MCF04, no protection against a challenge infection was obtained. These results again support our finding that the prosequence (proregion) or fragments thereof of cathepsin L is crucial for the induction of protection.

Amplification of a Unique Family of Cathepsin L Molecules from *F. hepatica* using NEJ-Specific Primers.

With primer set (i), the prosequence of cathepsin L was amplified, using adult *F. hepatica* cDNA as template. Three positive clones (da16, da12 and da13) were sequenced. Because of our primer choice, the clones started at nucleic acid 85 (Trp 21) and ended at na 381 (Tyr 119), according to the sequence as Wijffels et al. (1994). The sequences of the propeptide parts of these clones showed 96.5% to 98.4% homology to the sequence from Wijffels et al. (1994). The derived amino acid sequences showed 95.3% to 97.7% homology to the sequence of Wijffels et al. (1994).

With primer set (iii), the prosequence of cathepsin L was amplified, using cDNA from NEJs as template. Two PCR products were identified on agarose gel. The oligonucleotide with the expected size of 300 bp was pricked, amplified again using the same primers, and then ligated into the TA cloning vector. Of five different clones, the nucleotide sequences were determined. Forward and reverse sequence analysis revealed identical sequences. Clones da27, da26, da214 and da210 were very homologous, having 90.3% to 98.4% identities. These clones showed 79.5% to 82.2% homology to the prosequence (proregion) from Wijffels. The derived amino acid sequences showed 79.1% to 80.2% homology to the sequence from Wijffels. Clone da211 had a more different sequence and was more homologous (87.4) to the prosequence of Wijffels. The derived amino acid sequence showed 87.2% homology to the sequence from Wijffels. These data demonstrate that with the NEJ-specific primers a different "subfamily" of *F. hepatica* cathepsin L propeptides was amplified from NEJS, compared with the products amplified from adult *F. hepatica* using an adult *F. hepatica* specific primer set (16.6% to 23% discrepancies).

Moreover, the derived amino acid sequences from the "NEJ clones" reveal a significant change in the site where the prosequence from cathepsin L is cleaved off. In cathepsin L derived from adult *F. hepatica*, the prosequence is cleaved off between aa 106 and 107, with Arg at the P1 position, the uncharged polar Asn at the P2 position and Ala at the P1' position. In the four homologous cathepsin L clones obtained with the NEJ-specific primers, however, we found Asn at the P1 position, Asp or Gly at the P2 position and Asp at the P1' position. It is possible that other enzymes are needed to cleave off the propeptide of the "NEJ cathepsin L." This may result in a less efficient (auto)activation of the proprotein in the NEJ, compared with adult parasites. Since the prosequence is found essential for the induction of protection, this likely explains the high levels of protection obtained with NEJ antigens, compared with adult stage antigens. It may also explain the absence of an immunoreactive proprotein in antigen extract from adult *F. hepatica*, as demonstrated on immunoblot.

With primer sets (ii) and (iv) the entire procathepsin L was amplified with adult stage cDNA as template.

Cathepsin L Peptide ELISA for the Diagnosis of *F. hepatica* Infection in Cattle and Sheep Sera from two calves, sampled at regular intervals after infection with *F. hepatica*, were used to screen the peptide epitopes from cathepsin L (FIG. 4). No reactivity was observed with the peptide epitopes derived from the prosequence of cathepsin L, MCF03 and MCF06, and only low reactivity of one calve was detected with peptide MCL13. On the contrary, both calves gave a strong reaction with peptide MCF05 and especially peptide MCF04, from day 54 till at least day 154 after infection, comparable to the reaction obtained with purified cathepsin L. Combining of peptides MCF04 and MCF05 did not increase immunoreactivity. Accordingly, peptides MCF04 and MCF05 were specifically recognized by sera from four sheep (ten weeks after infection with *F. hepatica*).

Sera from 24 calves, monoinfected with *F. hepatica*, and from calves monoinfected with other, relevant parasites, were tested in the ELISA with peptide MCF04 and purified cathepsin L. All *F. hepatica* infected calves gave a positive reaction with both cathepsin L and peptide MCF04. On the contrary, neither of the calves infected with other, relevant parasites reacted with peptide MCF04. Accordingly, the D. Viviparus infected calves did not recognize peptide MCF04, whereas they gave a strong reaction with cathepsin L (cross-reactivity).

Peptide MCF04 was recognized by *F. hepatica* infected sheep from week 5 until at least week 16 after infection (FIG. 5). Panels of sera from sheep, infected with other, relevant parasites were also tested in the peptide ELISA (FIG. 5). Almost no reactivity of these sera with peptide MCF04 was detected.

These results demonstrate that an ELISA based on peptide MCF04 from cathepsin L is both sensitive and specific. We conclude that this ELISA is highly valuable for diagnostic purposes regarding *F. hepatica* infections, both for cattle and sheep. This peptide ELISA overcomes the problem of cross-reactivity, especially found with D. Viviparus infected calves. Moreover, because naturally infected calves and sheep do not recognize the protective peptide epitopes MCF03 and MCF06, the combination of MCF04 for diagnostic purposes and peptides such as MCF03/MCF06 for vaccination purposes has considerable potential for a vaccine.

PCR, Subcloning and Sequencing

To further study and obtain the isolated nucleotide sequence of a protective protein useful for vaccination against a wide range of parasitic infections, amplification, cloning and sequencing techniques known in the art are used. For example, in the case of the protective 30-32 kD protein of *Fasciola hepatica*, in a first step in RT-PCR, primers A and B are used. The sequence of primer A involves a set of degenerate oligonucleotides deduced from the N-terminal amino acid sequence. Primer B is, for example, deduced from a spliced leader sequence located upstream at the 5' end of parasitic mRNA (Davis et al., *The Journal of Biological Chemistry*, 31: 20026-20030, 1994). After amplification the obtained fragments are cloned and sequenced. A primer C is than selected located in the sequence between A and B and used together with a poly (dT) primer to amplify the corresponding 3' part of the wanted nucleotide sequence, after which the whole gene or selected fragments thereof are cloned and sequenced. By using the isolated nucleotide sequences in amplification or screening methods varying or different parasitic sequences that encode functionally equivalent proteins can be identified in and isolated from related parasites. All such nucleotide sequences or fragments thereof can be cloned by method known in the art in suitable expression systems to generate recombinant proteins that can be used in anti-parasite vaccines or for diagnostic purposes, as described above. Assessment of the protective value of such proteins can of course be performed in the ex vivo model provided by the invention. The nucleotide sequences alone, or incorporated in suitable vector systems or constructs can also be employed in DNA vaccination protocols.

REFERENCES

1. Bexter A. (1982). "Roulade"-technik/"Swiss-roll"-technik. *Histochemistry* 1:12-13.
2. Bitakaramire P. K. (1973). Preliminary studies on the immunization of cattle against fascioliasis using gamma-irradiated metacercariae of *Fasciola gigantica*. *Isotopes and Radiation in Parasitology III*. I. A. E. A. Vienna, 23-32.
3. Burden D. J., A. P. Bland, D. L. Hughes, and N. C. Hammet (1981). *Fasciola hepatica*: a technique for the study of gut penetration by juvenile flukes. *Parasitology* 83:249-252.
4. Burden D. J., E. Harness, and N. C. Hammet (1982). *Fasciola hepatica*: attempts to immunize rats and mice with metabolic and somatic antigens derived from juvenile flukes. *Veterinary Parasitology* 9:261-266.
5. Burden D. J., A. P. Bland, N. C. Hammet, and D. L. Hughes (1983). *Fasciola hepatica*: migration of newly excysted juveniles in resistant rats. *Experimental Parasitology* 56:277-288.
6. Dawes B. (1963). The migration of juvenile forms of *Fasciola hepatica* through the wall of the intestines in the mouse, with some observations on food and feeding. *Parasitology* 53:109-122.

7. Doy T. G., D. L. Hughes, and E. Harness (1978). Resistance of the rat to reinfection with *Fasciola hepatica* and the possible involvement of intestinal leucocytes. *Research in Veterinary Science* 25:41-44.

8. Doy T. G., D. L. Hughes, and E. Harness (1981). Hypersensitivity in rats infected with *Fasciola hepatica*: possible role in protection against challenge infection. *Research in Veterinary Science* 30:360-363.

9. Doy T. G. and D. L. Hughes (1982). Evidence for two distinct mechanisms of resistance in the rat to reinfection with *Fasciola hepatica*. *International Journal of Parasitology* 12:357-361.

10. Doy T. G. and D. L. Hughes (1984). *Fasciola hepatica*: site of resistance to reinfection in cattle. *Experimental Parasitology* 57:274-278.

11. Hall R. F. and B. Z. Lang (1978). The development of an experimental vaccine against *Fasciola hepatica* in cattle. *Proc. 82nd Ann. Meeting U.S. Anim. Health Assoc.*, Buffalo, N.Y.

12. A review. *Veterinary Parasitology* 20:63-93.

12A. Hayes T. J., J. Bailer, and M. Mitrovic (1973). Immunity to *Fasciola hepatica* in rats: the effect of two different levels of primary exposure on superinfection. *Journal of Parasitology* 59:810-812.

13. Hayes T. J. and M. Mitrovic (1977). The early expression of protective immunity to *Fasciola hepatica* in rats. *Journal of Parasitology* 63:584-587.

14. Hillyer G. V., E. T. M. Haroun, A. Hernandez, and M. Soler de Galanes (1987). Acquired resistance to *Fasciola hepatica* in cattle using a purified adult worm antigen. *Am. J. Trop. Med. Hyg.* 37:363-369.

15. Howell M. J., P. G. Board, and J. C. Boray (1988). Glutathione S-transferase in *Fasciola hepatica*. *J. Parasitol.* 74:715-718.

16. Johnson K. S., G. B. L. Harrison, M. W. Lightowlers, K. L. O'Hoy, W. G. Cougle, R. P. Dempster, S. B. Lawrence, J. G. Vinton, D. D. Heath, and M. D. Rickard (1989). Vaccination against ovine cysticercosis using a defined recombinant antigen. *Nature* 338:585-587.

17. Kawano J., T. Yamamoto, M. Koga, A. Shimizu, and S. Kimura (1992). Penetration in vitro of newly excysted juvenile flukes of Japanese *Fasciola* sp. through ligated intestines of rabbits, mice, rats and chickens. *Journal of Veterinary and Medical Science* 54:69-73.

18. Lang B. Z. and R. F. Hall (1977). Host-parasite relationships of *Fasciola hepatica* in the white mouse. VII. Successful vaccination with culture incubate antigens and antigens from somatic disruption of immature worms. *J. Parasitol.* 63:1046-1049.

19. Madsudaira (1987). *J. Biol. Chem.* 262:10035-10038.

20. McGonigle S. and J. P. Dalton (1995). Isolation of *Fasciola hepatica* haemoglobin. *Parasitology* 111:209-215.

20A. Moreau Y. (1986). Immunologie parasitaire: réalité perspectives. *Point Veterinaire* 18:467-473.

21. Newton S. E. (1995). Progress on vaccination against *Haemonchus concortus*. *Int. J. Parasitol.* 25(11):1281-1289.

22. Oldham G. and D. L. Hughes (1982). *Fasciola hepatica*: immunization of rats by intraperitoneal injection of adult fluke antigen in Freund's adjuvant. *Experimental Parasitology* 54:7-11.

23. Oldham G. (1983). Protection against *Fasciola hepatica* in rats with adult fluke antigen in Freund's adjuvant: influence of antigen batch, antigen dose and number of sensitizing injections. *Research in Veterinary Science* 34:240-244.

24. Peacock R. and D. Poynter (1980). Field experience with a bovine lungworm vaccine. In A. E. R. Taylor and R. Muller (Eds.), *Vaccines against parasites* 141-148. Oxford, Blackwell Scientific Publications.

25. Pfister K., K. Turner, and H. Wedrychowicz (1984/85). Worm recovery, hemagglutinating antibodies and IgE-levels after immunization against *Fasciola hepatica* in rats. *Veterinary Parasitology* 17:139-150.

26. Purnell R. (1980). Vaccines against piroplasms. In A. E. R. Taylor and R. Muller (Eds.), *Vaccines against parasites* 25-55. Oxford, Blackwell Scientific Publications.

27. Sexton J. L., A. R. Milner, M. Panaccio, J. Waddington, G. L. Wijffels, D. Chandler, C. Thompson, L. Wilson, T. W. Spithill, G. F. Mitchell, and N. J. Cambell (1990). Glutathione S-transferase: novel vaccine against *Fasciola hepatica* in sheep. *Journal of Immunology* 145:3905-3910.

28. Schagger H. and G. von Jagow (1987). *Anal. Biochem.* 166:368-379.

29. Sharma R. L., T. K. Bhat, and D. N. Dhar (1988). Control of sheep lungworm in India. *Parasitology Today* 4:33-36.

30. Smith A. M., A. J. Dowd, S. McGonigle, P. S. Keegan, G. Brennan, A. Trudgett, and J. P. Dalton (1993). Purification of a cathepsin L-like proteinase secreted by adult *Fasciola hepatica*. *Molecular and Biochemical Parasitology* 62:1-8.

31. Smith A. M., C. Carmona, A. J. Dowd, S. McGonigle, D. Acosta, and J. P. Dalton (1994). Neutralization of the activity of a *Fasciola hepatica* cathepsin L proteinase by anti-cathepsin L antibodies. *Parasite Immunology* 16:325-328.

32. Smith M. A. and J. A. Clegg (1981). Improved culture of *Fasciola hepatica* in vitro. *Zeitschrift für Parasitenkunde* 66:9-15.

33. Spithill T. W. (1995). Vaccines for control of *Fasciola hepatica* infection in ruminants. Abstract at the *8th Intern. Congress of Parasitology*, 10-14 Oct. 1995, Izmir, Turkey.

34. Tanner M., T. Teuscher, and P. L. Alonso (1995). SPf66— The first malaria vaccine. *Parasitology Today* 11: 10-13.

34A. Taylor M. G., Q. D. Bickle, S. L. James, and A. Sher (1986). Irradiated schistosome vaccines. *Parasitology Today* 2:132-134.

35. Tendler M., C. A. Brito, M. M. Vilar, N. Serra-Freire, D. M. Diogo, M. S. Almeida, A. C. Delbem, J. F. Da-Silva, W. Savino, R. C. Garratt, N. Katz, and A. J. G. Simpson (1996). A *Schistosoma mansoni* fatty-binding protein, Sm 14, is the potential basis of a dual-purpose anti-helminth vaccine. *Proc. Natl. Acad. Sci. USA* 93:269-273.

36. Tkalcevic J., K. Ashman, and E. Meeusen (1995). *Fasciola hepatica*: rapid identification of newly excysted juvenile proteins. *Biochemical and Biophysical Research Communications* 213:169-174.

37. Urquhart G. M. (1980). Immunity to cestodes. In A. E. R. Taylor and R. Muller (Eds.), *Vaccines against parasites* 107-114. Oxford, Blackwell Scientific Publications.

38. Zahner H. (1994). Workshop summary: vaccine development. *Veterinary Parasitology* 54:327-330.

39. Wijffels G. L., M. Panaccio, L. Salvatore, L. Wilson, I. D. Walker, and T. W. Spithill (1994). The secreted cathepsin L-like proteinases of the trematode, *Fasciola hepatica*, contain 3-hydroxyproline residues. *Biochem. J.* 299:781-790.

40. Fields C. G., D. H. Lloyd, R. L. Macdonald, K. M. Otteson, and R. L. Noble (1991). *Peptide Research* 4:95.

41. Dalton J. P. and M. Heffernan (1989). Thiol proteases released in vitro by *Fasciola hepatica*. *Molecular and Biochemical Parasitology* 35:161-166.

42. Berasain P., F. Goni, S. McGonigle, A. Dowd, and J. P. Dalton (1997). Proteinases secreted by *Fasciola hepatica* degrade extracellular matrix and basement membrane components. *J. Parasitology* 83:1-5.
43. Smith A. M., A. J. Dowd, M. Heffernan, C. D. Robertson, J. P. Dalton (1993). *Fasciola hepatica*: A secreted cathepsin L-like proteinase cleaves host immunoglobulin. *Int. J. Parasitol.* 23:977-983.
44. C. Carmona, A. J. Dowd, A. M. Smith, and J. P. Dalton (1993). Cathepsin, L proteinase secreted by *Fasciola hepatica* in vitro prevents antibody-mediated eosinophil attachment to newly excysted juveniles. *Mol. Biochem. Parasitol.* 62:9-18.
45. North M. J., J. C. Mottram, and G. H. Coombs (1990). Cystein proteinases of parasitic protozoa. *Parasitology Today* 6:270-275.
46. Sanger F., S. Niklen, and A. R. Coulson (1977). DNA sequencing with chain-terminating inhibitors. *Proceedings of the National Academy of Sciences, USA* 74:5463-5467.
47. Dalton J. P., S. McGonicle, T. P. Rolph, and S. J. Andrews (1996). Induction of protective immunity in cattle against infection with *Fasciola hepatica* by vaccination with cathepsin L proteinases and with hemoglobin. *Infection and Immunity* 64:5060-5074.
48. Morrison C. A., T. Colin, J. L. Sexton, F. Bowen, J. Wicker, T. Friedel, and T. W. Spithill (1996), Protection of cattle against *Fasciola hepatica* infection by vaccination with glutathion S-transferase. *Vaccine* 14:1603-1612.
49. Dowd A. J., A. M. Smith, S. McGonigle, and J. P. Dalton (1994). Purification and characterization of a second cathepsin L proteinase secreted by the parasitic trematode *Fasciola hepatica*. *Eur. J. Biochem.* 223:91-98.
50. de Leeuw W. A. and J. B. W. J. Cornelissen (1993). Comparison of three enzyme immunoassays for diagnosis of *Dictyocaulus viviparus* infection. *Vet. Parasitol.* 49:229-41.
51. Day S. R. D. and P. B. J. Brindley (1995). Characterization and cloning of the cathepsin L proteinases of *Schistosoma japonicum*. *Biochem. Biophys. Res. Commun.* 217:(1), 11-19.
52. Smith A. M., J. P. Dalton, K. A. Clough, C. L. Kilbane, S. A. Harrop, N. Hole, and P. J. Brindley (1994). Adult *Schistosoma mansoni* express cathepsin L proteinase activity. *Mol. Biochem. Parasitol.* 67:11-19.
53. Michel A., M. Klinkert, and W. Kunz (1994). *EMBL Data Library*.
54. Joseph L. J., L. C. Chang, D. Stamenkovich, and V. P. Sukhatme (1988). Complete nucleotide and deduce amino acid sequences of human and murine preprocathepsin L. An abundant transcript induce by transformation of fibroblasts. *J. Clin. Invest.* 81:(5), 1621-1629.

What is claimed is:

1. An isolated or recombinant protective protein derived from a proregion of a cathepsin-like protease that is specific for a newly excysted juvenile (NEJ) stage of *Fasciola hepatica* wherein the protein comprises the amino acid sequence selected from the group consisting of SEQ ID NO:1, SEQ ID NO:24, and SEQ ID NO:26.

2. The isolated or recombinant protective protein according to claim 1, as shown to be protective in a method comprising using an ex vivo animal or challenge model to measure protective immunity directed against a parasite.

3. The protective protein of claim 1, wherein said protein is a recombinant protein.

4. A vaccine comprising the protective protein of claim 1.

5. The vaccine of claim 4 further comprising a pharmaceutically acceptable vehicle.

6. The vaccine composition of claim 5, wherein said protective protein is recombinant.

7. A diagnostic test comprising: the protective protein of claim 1 and a molecule to detect immune complexes between the protective protein of claim 1 and antibodies from a sample of a subject to be tested.

8. A method for immunizing an animal against infection by *Fasciola hepatica*, the method comprising administering to the animal the vaccine composition of claim 5.

9. The method according to claim 8, wherein *Fasciola hepatica* is of the type that infects a host through a mucosal or skin surface.

* * * * *